(12) United States Patent
Chung et al.

(10) Patent No.: US 11,719,585 B2
(45) Date of Patent: Aug. 8, 2023

(54) FIBER-BASED COMPOSITE WITH FRACTURE-INDUCED MECHANO-ELECTRICAL SENSITIVITY

(71) Applicant: UNIVERSITY OF WASHINGTON, Seattle, WA (US)

(72) Inventors: Jae-Hyun Chung, Seattle, WA (US); Jinyuan Zhang, Seattle, WA (US); Dayong Gao, Seattle, WA (US); Jinkyu Yang, Seattle, WA (US)

(73) Assignee: University of Washington, Seattle, WA (US)

( * ) Notice: Subject to any disclaimer, the term of this patent is extended or adjusted under 35 U.S.C. 154(b) by 293 days.

(21) Appl. No.: 16/768,373

(22) PCT Filed: Dec. 3, 2018

(86) PCT No.: PCT/US2018/063645
§ 371 (c)(1),
(2) Date: May 29, 2020

(87) PCT Pub. No.: WO2019/109085
PCT Pub. Date: Jun. 6, 2019

(65) Prior Publication Data
US 2020/0370972 A1    Nov. 26, 2020

Related U.S. Application Data

(60) Provisional application No. 62/593,774, filed on Dec. 1, 2017.

(51) Int. Cl.
*C01B 32/158* (2017.01)
*G01L 1/18* (2006.01)
(Continued)

(52) U.S. Cl.
CPC ............... *G01L 1/18* (2013.01); *G01L 1/142* (2013.01); *A61B 5/1125* (2013.01); *A61B 5/682* (2013.01);
(Continued)

(58) Field of Classification Search
CPC ......... G01L 1/18; G01L 1/142; A61B 5/1125; A61B 5/682; A61B 5/6821; A61B 5/6823; A61B 5/6826; H01L 51/444
(Continued)

(56) References Cited

U.S. PATENT DOCUMENTS

| | | | |
|---|---|---|---|
| 2008/0170982 A1* | 7/2008 | Zhang | H01L 51/444 423/447.3 |
| 2010/0173228 A1 | 7/2010 | Wallace et al. | |

(Continued)

FOREIGN PATENT DOCUMENTS

KR    1020130084832 A    7/2013

OTHER PUBLICATIONS

Office Action dated Mar. 29, 2022, issued in corresponding Chinese Application No. 201880077381.X, filed May 29, 2020, 16 pages.
(Continued)

*Primary Examiner* — Abdul-Samad A Adediran
(74) *Attorney, Agent, or Firm* — Christensen O'Connor Johnson Kindness PLLC

(57) ABSTRACT

Fracture-induced composite sensors and methods of their fabrication are disclosed. The sensors can be used as strain sensors, piezo-resistive sensors, piezo-capacitive sensors, and non-contact displacement wearable sensors.

20 Claims, 25 Drawing Sheets

(51) Int. Cl.
  *G01L 1/14*    (2006.01)
  *A61B 5/11*    (2006.01)
  *A61B 5/00*    (2006.01)

(52) U.S. Cl.
  CPC ........... *A61B 5/6821* (2013.01); *A61B 5/6823* (2013.01); *A61B 5/6826* (2013.01)

(58) Field of Classification Search
  USPC ...................................................... 423/447.3
  See application file for complete search history.

(56)         References Cited

U.S. PATENT DOCUMENTS

| | | |
|---|---|---|
| 2010/0294976 A1 | 11/2010 | Ajayan et al. |
| 2012/0111599 A1 | 5/2012 | Roberson et al. |
| 2013/0031987 A1 | 2/2013 | Beauvais et al. |
| 2014/0026678 A1 | 1/2014 | Cannard et al. |
| 2014/0331793 A1 | 11/2014 | Suzuki et al. |
| 2015/0240391 A1 | 8/2015 | Oh et al. |
| 2016/0251498 A1 | 9/2016 | Imai et al. |

OTHER PUBLICATIONS

First Examination Report dated Mar. 7, 2022, issued in corresponding Indian Application No. 202047026175, filed Jun. 22, 2020, 7 pages.
International Search Report and Written Opinion, in corresponding International Patent Application No. PCT/US2018/63645, 10 pages.
Notice of Grant dated Feb. 14, 2023, issued in corresponding Chinese Application No. 201880077381.X, filed Dec. 3, 2018, 3 pages.

\* cited by examiner

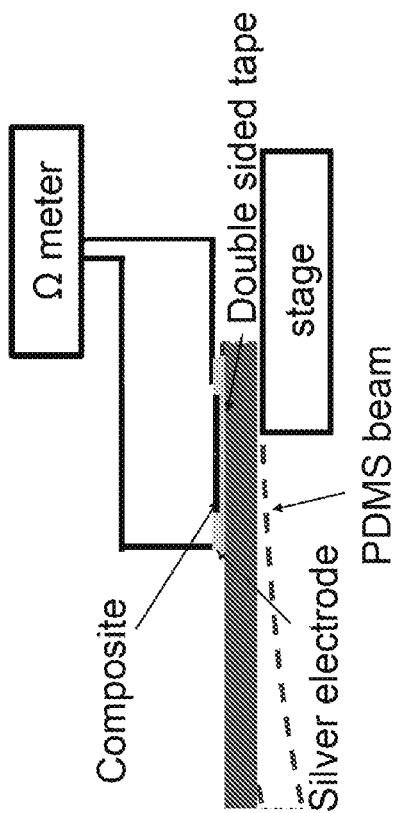
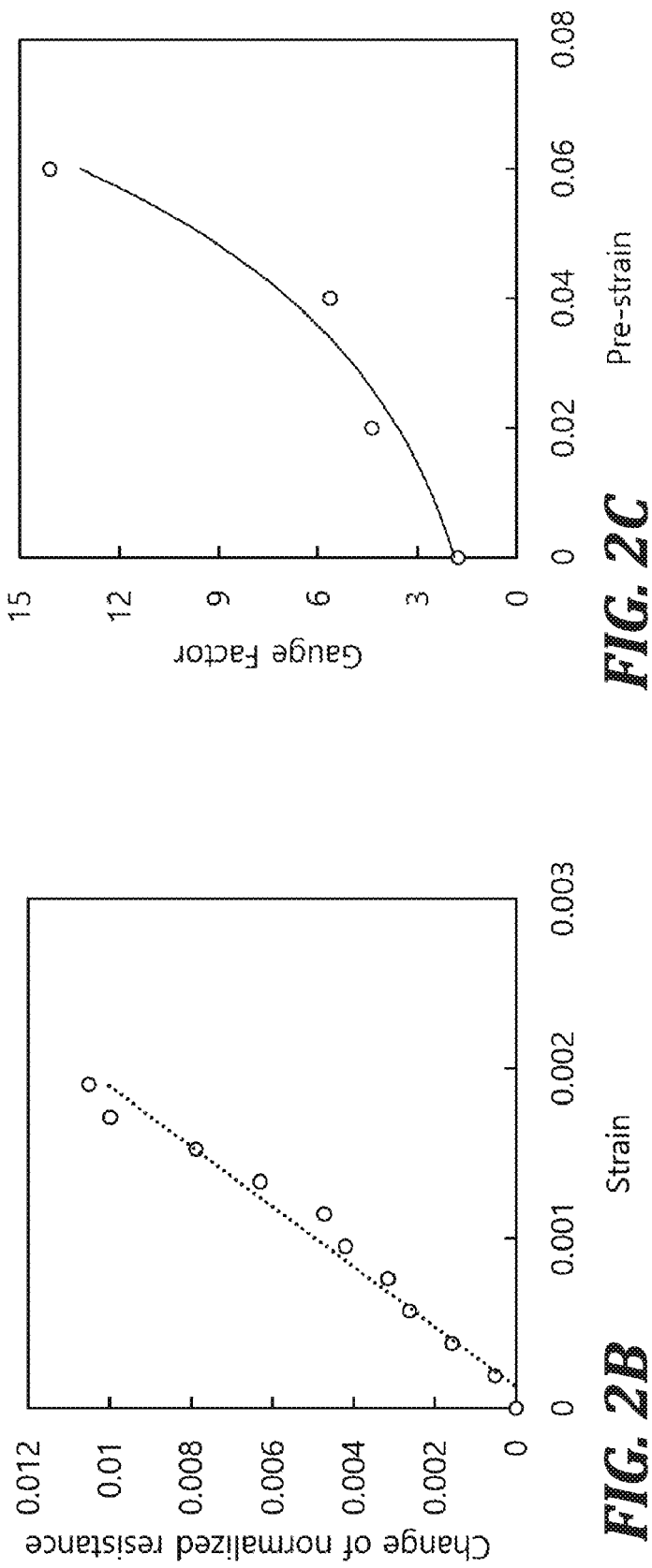
FIG. 2A
FIG. 2B
FIG. 2C

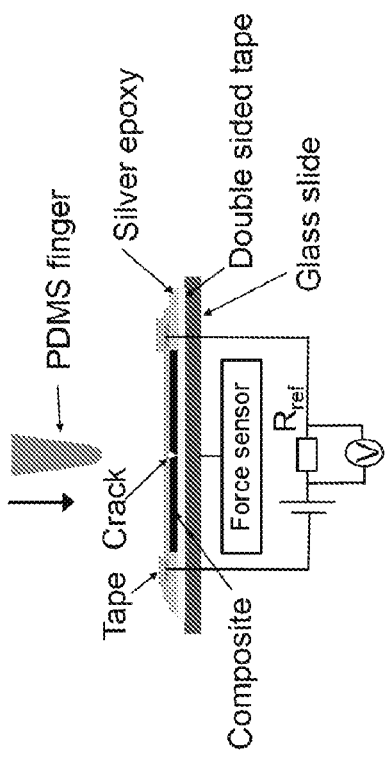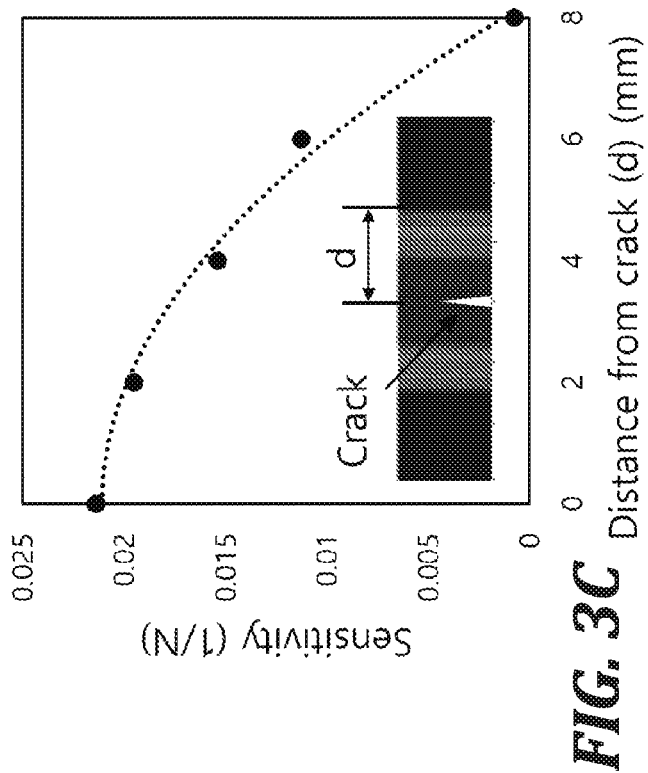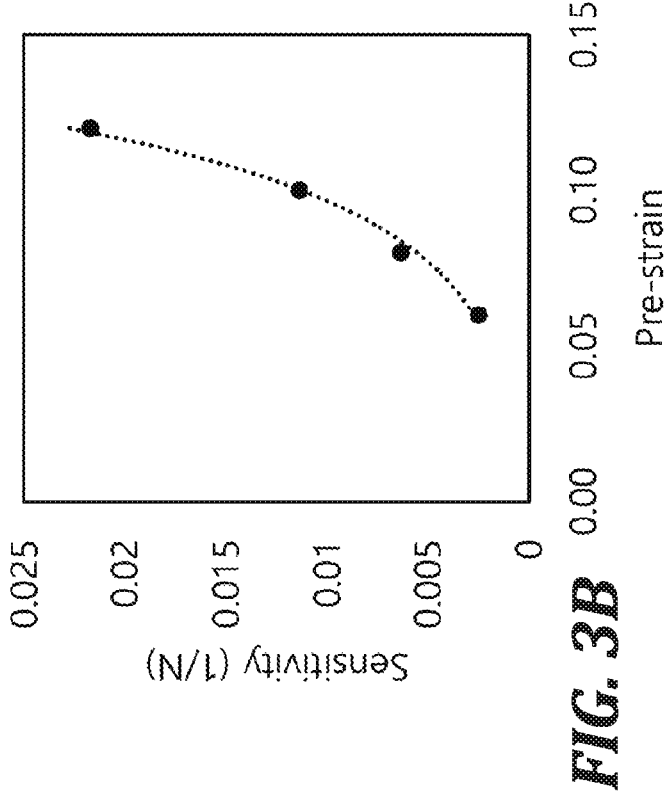
FIG. 3A
FIG. 3B
FIG. 3C

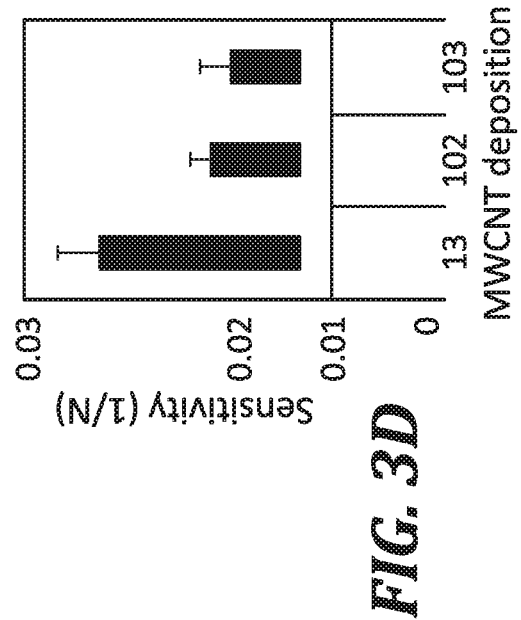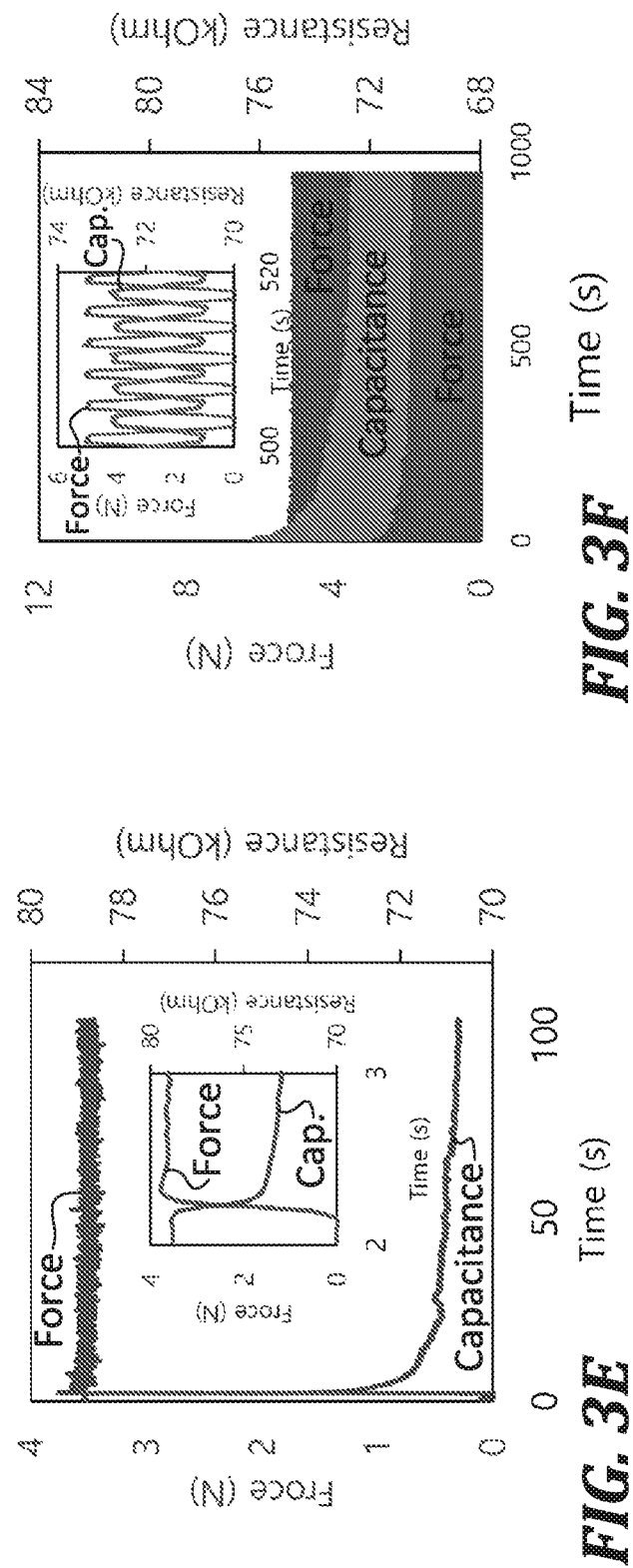
FIG. 3D
FIG. 3E
FIG. 3F 3 times coated paper plain paper 20 times coated paper 10 times coated paper

FIBER-BASED COMPOSITE WITH FRACTURE-INDUCED MECHANO-ELECTRICAL SENSITIVITY

CROSS-REFERENCE TO RELATED APPLICATION

This application claims the benefit of U.S. Provisional Application No. 62/593,774, filed Dec. 1, 2017, the disclosure of which is expressly incorporated herein by reference in its entirety.

BACKGROUND

Wearable sensors have both diagnostic and monitoring applications. Recent developments in materials, electronics, and manufacturing techniques enabled the development of new high-fidelity sensing platforms and their applications in the biomedical field. For example, eye movement tracking sensors can be used for the diagnosis and treatment of neurological diseases, such as epilepsy, autism, and dementia. However, current wearable sensors are limited in usability, accessibility, and cost. Bulky equipment and high operation costs significantly limit the accessibility and clinical applications of the technology.

Nanostructured composites using cellulose fiber templates have shown promise for development of light-weight and inexpensive sensing devices. Cellulose fibers extracted from wood pulp offer large surface area, facilitating energy, sensing, and electronic applications. Since the porous and hydrophilic nature of cellulose fibers enhances adhesion, various nanomaterials have been used to modify the surface properties of cellulose fibers for multifunctionality. Carbon nanotubes (CNTs) are versatile filler materials to create electrical and thermal conductivity. When a CNT-paper composite (CPC) is fabricated, it promises novel applications, such as flexible electronics, energy devices, and sensors. However, the random network of CNTs in a cellulose fiber matrix limits the mechanoelectrical sensitivity due to the numerous current paths in the matrix.

Thus, a need still exists for a low cost, preferably disposable, easily accessible sensor which can be easily adapted to the human body for behavior monitoring.

SUMMARY

In one aspect, provided herein is a sensor, comprising:
a composite substrate comprising a template material comprising a plurality of insulating fibers and a plurality of carbon nanotubes bonded to the insulating fibers forming a nanotube coating on the insulating fibers, the composite substrate having a fracture induced by application of a unidirectional tensile force to the composite substrate, wherein the plurality of insulating fibers form a plurality of crossbar junctions at the site of the fracture; and
a first electrode coupled to the nanotube coating on one side of the fracture and a second electrode coupled to the nanotube coating on the opposite side of the fracture, such that an electrical signal applied between the first electrode and the second electrode passes through the plurality of crossbar junctions at the site of the fracture.

In another aspect, provided herein is a method of making a sensor comprising applying a unidirectional tensile force to a precursor composite substrate thereby inducing a fracture to form a fractured composite substrate, wherein the precursor composite substrate comprises:
a template material comprising a plurality of insulating fibers;
a plurality of carbon nanotubes bonded to the insulating fibers forming a nanotube coating on the insulating fibers;
a first electrode coupled to the nanotube coating on one side of the fracture; and
a second electrode coupled to the nanotube coating on the opposite side of the fracture; and
wherein the plurality of insulating fibers form a plurality of crossbar junctions at the site of the fracture.

In some embodiments, the carbon nanotubes are multi-wall carbon nanotubes. In some embodiments, the insulating fibers are fibers extracted from wood pulp, cotton fibers, synthetic fiber, or a combination thereof.

In another aspect, methods of using a sensor, as shown and described herein, are provided. In some embodiments, the sensors disclosed herein can be used as in-plane strain sensors, out-of-plane piezo-resistive sensors, or capacitive sensors.

DESCRIPTION OF THE DRAWINGS

FIG. 1 is a schematic of the fabrication process. FIG. 1B is a conceptual illustration of the sensitivity generation according to mechanical and electrical properties. FIG. 1C shows stress-strain characteristics (left) and relative resistance change (right) for plain paper and composites with 3×, 10×, and 20× carbon nanotube depositions; with stretching perpendicular to the dominant fiber orientation. FIG. 1D shows schematics of the micro and nano structure reorientation of the composite, SEM images, and orientation statistics according to the applied strain.

FIGS. 2A-2C illustrate evaluation of an exemplary strain sensor in stage II. FIG. 2A shows schematics of the strain sensor design and calibration. FIG. 2B shows normalized resistance change according to the applied strain by bending (pre-strain: 0.04 mm/mm; 3× multi-wall carbon nanotubes (MWCNT) depositions). FIG. 2C shows gauge factor according to the pre-strain that is applied for a carbon nanotube-paper composite (CPC).

FIGS. 3A-3F illustrate evaluation of an exemplary piezo-resistive force sensor in stage III. FIG. 3A is schematics of piezo-resistive force sensor calibration. Force and voltage are recorded when the cracked area of a sensor is pressed by a PDMS finger. Inset is the picture of the testing setup. FIG. 3B is sensitivity variation for various applied pre-strain. FIG. 3C is sensitivity variation for different locations on a cracked sensor. In the inset figure, 'd' denotes the distance between the crack tip and the measurement location. FIG. 3D is sensitivity variation for 3×, 10×, and 20×MWCNT depositions. FIG. 3E shows resistance response to a step force input of 3.5 N. Inset shows the close-up of the response time. FIG. 3F is resistance variation for cyclic loading (0.3 Hz). Inset: close-up of the electrical response for 500~520 seconds.

FIG. 4A shows schematics of piezo-capacitive force sensor calibration. Force and capacitance are recorded when the cracked surface of the sensor is pressed. FIG. 4B shows normalized capacitance change for both conductive and non-conductive object for CPC of 3×MWCNT depositions. FIG. 4C shows capacitance response to a step force input of 8 N. Inset: close-up of the response time. FIG. 4D shows capacitance change of non-contact displacement as a function of the distance between the sensor and a conductive object. FIG. 4E shows capacitive response of a noncontact displacement sensor to cyclic displacement by a piezo-actuator (8 μm). FIG. 4F shows capacitive change of a conductive PDMS finger for a cyclic force. Inset: close-up of the capacitive change between 500~520 seconds.

FIG. 5A shows a resistive heart beat sensor on wrist. FIG. 5B shows a capacitive heartbeat sensor on wrist. FIG. 5C shows a haptic force sensor attached on a glove. FIG. 5D shows monitoring of bending of a finger using a sensor attached on a glove. FIG. 5E shows a non-contact capacitive sensor for eyeball and eyelid movement and capacitive response for open/close eye lid and up/down eyeball movement. FIG. 5F shows a non-contact capacitive sensor for lip movement and capacitive response to speaking "one" and "two."

DETAILED DESCRIPTION

Figure 1A:
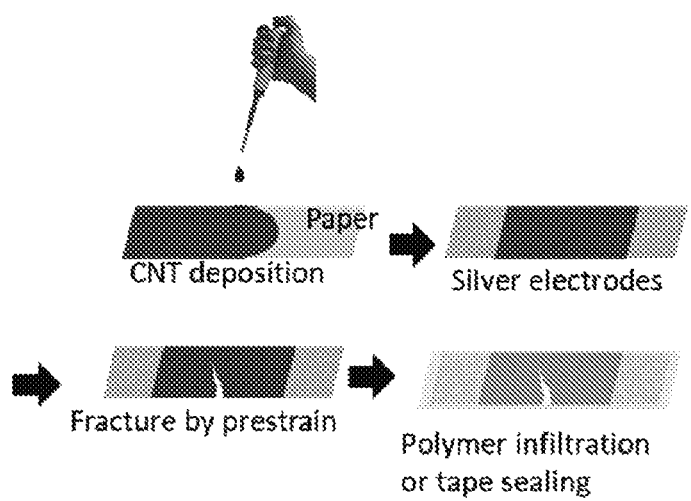
FIGS. 1A-1D illustrate the fabrication process and mechanism of tensile fracture-induced sensors.

Disclosed herein are fracture-induced composite sensors and methods of forming thereof. When strain is applied to a composite material comprising template substrate comprising a plurality of insulating fibers, such as cellulose fibers, and carbon nanotubes bonded to the template substrate, the carbon-nanotube coated cellulose fibers are aligned to form cross junctions with the breakage of the template substrate fibers in the stretching direction. Depending on the applied strain, the resulting fractured composite can be used as a piezo-resistive sensor, piezo-capacitive sensor, or non-contact displacement sensor. Using this manufacturing method, thin and flexible novel wearable sensors can be produced inexpensively. Representative uses for the sensors include human-movement tracking.

Thus, in one aspect, provided herein is a fracture-induced composite carbon nanotube sensor. In some embodiments, the sensor comprises (a) a composite substrate comprising a template material comprising a plurality of insulating fibers and a plurality of carbon nanotubes bonded to the insulating fibers forming a nanotube coating on the insulating fibers, the composite substrate having a fracture induced by application of a unidirectional tensile force to the composite substrate, wherein the plurality of insulating fibers form a plurality of crossbar junctions at the site of the fracture; and (b) a first electrode coupled to the nanotube coating on one side of the fracture and a second electrode coupled to the nanotube coating on the opposite side of the fracture, such that an electrical signal applied between the first electrode and the second electrode passes through the plurality of crossbar junctions at the site of the fracture.

In some embodiments, the sensor comprises template material comprising insulating fibers. As used herein, the term "insulating" refers to a material that has electrical resistance greater than about 1 GΩ ($10^9$ Ω). Exemplary template materials include a woven fiber mat, such as a cellulose mat, tissue, or porous paper. Any suitable insulating fibers can be used in the template material. For example, in some embodiments, the insulating fibers are fibers extracted from wood pulp, cotton fibers, synthetic fibers, or a combination thereof. Carbohydrate fibers, such as cellulose fibers, are particularly suitable for inclusion in the sensors disclosed herein. In some embodiments, the template material is a cellulose fiber matrix. In other embodiments, the template material can comprise fibers prepared from an insulating synthetic polymer. In some embodiments, the template material comprises tensional directional fibers which can be stretched to induce a crack or a fracture in the material.

In some embodiments, the template material has a thickness in the range of about 0.1 microns to about 10,000 microns, about 0.1 micron to about 1,000 microns, about 0.1 micron to about 500 microns, or about 0.1 microns to about 100 microns. Throughout the disclosure, any approximate terms, such as "about," "approximately," and "substantially," indicate that the subject can be modified by plus or minus 5% and fall within the described embodiment.

In some embodiments, the insulating fibers of the template material have a diameter between about 10 nm and about 100 μm, between about 10 nm and about 75 μm, or between about 10 nm and about 50 μm. In some embodiments, the insulating fibers have a curvature radius larger than 10 μm.

In certain embodiments, the sensor comprises a plurality of carbon nanotubes deposited on the insulating fibers of the template material. In some embodiments, the carbon nanotubes are multi-wall carbon nanotubes. In some embodiments, the carbon nanotubes have a diameter in the range of about 0.5 nm to about 200 nm, about 0.8 nm to about 200 nm, about 1 nm to about 100 nm, or about 0.8 nm to about 10 nm. In some embodiments, the carbon nanotubes have a length between about 0.1 μm and about 100 μm, between about 0.1 μm and about 50 μm, between about 1 μm and about 50 μm, between about 10 μm and about 100 μm.

In some embodiments, the carbon nanotubes, for example, multi-walled carbon nanotubes (MWCNTs), are bound to the insulating fibers by hydrogen bonding, ionic bonding, covalent bonding, nonspecific bonding, or a combination thereof. In some embodiments, the carbon nanotubes are deposited on the insulating fibers when a suspension of carbon nanotubes is drawn into the template material by capillary forces. In some embodiments, one or more depositions of carbon nanotubes on the insulating fibers can be used to prepare the sensors disclosed herein, for example, 1, 3, 5, 10, or 20 depositions. In some embodiments, the carbon nanotubes are deposited on the fibers from an aqueous suspension of multiwall carbon nanotubes that can optionally comprise a surfactant. Any suitable surfactant can be used for preparation of the carbon nanotube suspensions useful for the preparation of the sensors disclosed herein.

In some embodiments, the sensor comprises a first electrode coupled to the nanotube coating on one side of the fracture and a second electrode coupled to the nanotube coating on the opposite side of the fracture, such that an electrical signal applied between the first electrode and the second electrode passes through the plurality of crossbar junctions at the site of the fracture. In some embodiments, the electrodes comprise electrically conductive material. The electrodes can be applied to the nanotube coating by applying electrically conductive epoxy to the composite substrate. In some embodiments, the electrodes are silver.

In some embodiments, the sensor can be optionally attached to a support or a substrate material. Any suitable material can be used as a support material for the sensors disclosed herein. Examples of support materials include paper, polymeric materials, or combinations thereof. Attachment of the sensor to the support material can be achieved in any suitable manner, for instance, the substrate material can be attached using tape, glue, infiltrating polymer, filler material, or a combination thereof.

In some embodiments, the sensors comprise a fracture induced by application of a unidirectional tensile force to the composite substrate. In some embodiments, the plurality of the insulating fibers forms a plurality of crossbar junctions (also referred to as "crossing junctions") at the site of the fracture. As used herein, the term "crossbar junctions" refers to the junctions made of multiple crossing insulating fibers coated with carbon nanotubes. In some embodiments, the composite substrate comprises fibers which are oriented parallel, perpendicular, and at incline to the application of force. As shown in FIG. 1D, when strain is applied to the composite substrate, the parallel fibers begin to straighten and stiffen in the direction of the applied force. The resistance of the composite substrate increases due to the breakage of the carbon nanotube bridges spanning neighboring fibers. As the strain increases, the majority of parallel fibers are fractured at an ultimate strength, and the nanotubes bonded to the fibers are fractured as well. The perpendicular and inclined fibers begin to reorganize and form numerous cross-shaped junctions, as shown in FIGS. 13 and 14A-14D. Electrical resistance of the substrate increases exponentially as the carbon nanotube network of the fractured fibers is broken.

In some embodiments, the sensors are strain sensors, piezo-resistive sensors, or capacitive sensors. In some embodiments, the sensor types are determined by the applied strain. In some embodiments, the sensors are fabricated to exploit different sensing mechanisms by the magnitude of applied pre-strain. To induce the fracture, in some embodiments, a composite substrate specimen (e.g., carbon nanotube-paper composite) is fixed, and the tensile stress is applied. The force and resistance (or voltage) of composite substrate is recorded during the stretching. Typically, the stress-strain relationship shows three different stages in terms of the mechanical and electrical behavior of the composite substrates disclosed herein, as shown in FIG. 1B.

The electrical resistance at the initial stage ($I_0$) increases linearly at the elastic region (stage II in FIG. 1B) by uni-directional strain. With the application of larger strain, a crack is initiated and propagated orthogonally to the applied tension, which significantly reduces the mechanical stiffness of composite substrate (stage III in FIG. 1B). The electrical resistance increases substantially due to the fracture of carbon nanotube-coated insulating fibers. Near the crack, the untangled carbon nanotube-coated insulating fibers form crossbar junctions where the carbon nanotubes exhibit out-of-plane piezo-resistivity. Thus, the composite substrate at this stage can be used in an out-of-plane piezo-resistive sensor. With larger strain, the increased stress near the crack tip terminates the composite electrically (Resistance>500MΩ) (stage IV in FIG. 1B), while the composite is still connected by untangled fibers. Thus, the composite substrate at this stage can be used in an out-of-plane piezo-capacitive sensor.

In some embodiments, the slope of the stress-strain curve and electrical resistance of the composite substrate can be indicative of the type of the sensor disclosed herein. In some embodiments, the sensing mechanism, including, but not limited to, in-plane strain sensor, out-of-plane piezo-resistive sensor, and capacitive sensor, is defined by the magnitude of applied pre-strain and electrical resistance. In some embodiments, when the slope of the stress-strain curve is positive, the sensor is a strain sensor. In some embodiments, when the slope of the stress-strain curve is negative, the sensor is a piezo-resistive sensor. In some embodiments, when the resistance of the composite substrate is greater than about 100MΩ or infinite, the sensor is a capacitive sensor.

The sensors disclosed herein can be configured for use to monitor human behavior. In some embodiments, the sensor is a heartbeat sensor, gripping motion sensor, finger movement sensor, an eye movement sensor, mouth movement sensor, or abdominal movement sensor. In some embodiments, the sensors are wearable sensors. The sensor disclosed herein can be disposable and/or comprise materials that are biodegradable.

In one embodiment, a heartbeat sensor is provided, comprising a sensor as disclosed herein. In one embodiment, a hand-motion sensor is provided, comprising a sensor as disclosed herein. In one embodiment, an eye-tracking sensor is provided, comprising a sensor as disclosed herein. In one embodiment, a lip movement sensor is provided, comprising a sensor as disclosed herein. The lip movement sensor can be a speaking sensor or a silent sensor.

In certain embodiments, the sensors are connected to a power supply and a monitoring system, such as a capacitance or resistance meter. The power supply and monitoring system can be housed in the same unit or separated. In further embodiments, an analytical component is provided that is programmed to interpret measurements provided by the monitoring system and translate the measurements so as to determine the nature of the movement that produced the measurements (e.g., the movement of a finger or an eye in a certain direction). The analytical component may be trained to interpret measurements by mapping known actions with the response generated (and measured) by those actions.

In a second aspect, provided herein is a method of manufacturing of a fracture-induced sensor disclosed herein. In some embodiments, the method comprises applying a unidirectional tensile force to a precursor composite substrate thereby inducing a fracture to form a fractured composite substrate, wherein the precursor composite substrate comprises:

a template material comprising a plurality of insulating fibers;

a plurality of carbon nanotubes bonded to the insulating fibers forming a nanotube coating on the insulating fibers;

a first electrode coupled to the nanotube coating on one side of the fracture; and a second electrode coupled to the nanotube coating on the opposite side of the fracture; and wherein the plurality of insulating fibers form a plurality of crossbar junctions at the site of the fracture.

In some embodiments, the method further comprises attaching the fractured composite substrate to a substrate material. Any suitable substrate materials and methods of attachment can be used in the methods disclosed herein, for example, a fractured composite substrate can be attached to a substrate material with glue, tape, infiltrating polymer, filler material, or a combination thereof.

In some embodiments, the method further comprises folding, rolling, or wrapping the fractured composite substrate, for example, to reduce the sensor size.

In some embodiments applying a composition comprising carbon nanotubes to the template material is followed by applying the first electrode and the second electrode. Any suitable materials can be used to apply the electrodes to the substrate.

The precursor composite substrate can be formed in any suitable manner, for example, by applying a composition comprising carbon nanotubes and an optional surfactant to the template material by capillary action, by dipping the template material into a composition comprising carbon nanotubes. Alternatively, the precursor composite substrate can be formed by binding carbon nanotubes to insulating fibers to form carbon nanotube-coated insulating fibers and then forming the composite substrate from the carbon nanotube-coated insulating fibers.

In some embodiments of the methods disclosed herein, the carbon nanotubes are multi-wall carbon nanotubes. In some embodiments, the composition comprising carbon nanotubes is an aqueous suspension of carbon nanotubes. The aqueous suspensions used in the methods disclosed herein can further comprise one or more surfactants, buffers, salts, or similar components. In some embodiments, the carbon nanotubes can comprise one or more reactive groups and can be covalently bound to the template material via formation of a covalent bond. Chemistries for covalent coupling are known in the art.

In some embodiments, the template material can be coated by repeatedly applying a composition comprising carbon nanotubes to the template material. In some embodiments, this application can be repeated at least 3, at least 10, or at least 20 times.

In another aspect, methods of using a sensor, as shown and described herein, are provided.

The following examples are included for the purpose of illustrating, not limiting, the described embodiments.

EXAMPLES

Fabrication of Exemplary Composite

An aqueous solution of MWCNTs (Nano structured & Amorphous Materials, Inc) was prepared by using 1% sodium dodecyl sulfate (SDS) in deionized water. After 2 hour-sonication, the solution was deposited on a suspended paper using a pipette. The CPC was cut into pieces (10×30 mm$^2$). For electrodes, silver epoxy (MG chemical #8330s-21G) was pasted onto both ends of the composite for a 10×10 mm$^2$ area. The specimen was cured in an oven at 65° C.

Mechanical and Electrical Tests

The nanocomposites were tested by using a custom-made uniaxial tensile test bed that was controlled by using LabView interface. The force and displacement were recorded for stress-strain relationship. Real-time, high-resolution video was used to observe the nanocomposite's behavior as well as its morphologies and failures under mechanical loading. The resolutions of the force and displacement sensors were 3 mN and 1 μm, respectively. The resistance was measured by using a reference resistor as shown in FIG. 3A.

Pre-Straining for Sensor Fabrication

The composite was stretched on the uniaxial tensile stage until the required strain value or resistance was reached. At a controlled value, the stage was stopped for 1 minute for structural stability of a composite. After the pre-straining, the composite was carefully unloaded from the setup and used for measurement.

Discussion of Results

With precise control of the applied strain under uni-axial load to a CNT-paper composite (CPC), the tensile directional fibers coated with CNTs were fractured, and the cellulose fibers inclined or orthogonal to the tension were reoriented to form crossbar junctions near a crack. The junctions created highly sensitive resistive and capacitive responses for measuring strain, force, and non-contact displacement. This novel manufacturing process allows the integration of flexible sensors in low-cost tissue paper, which is easily adapted to a human body for behavior monitoring.

Figure 1B:
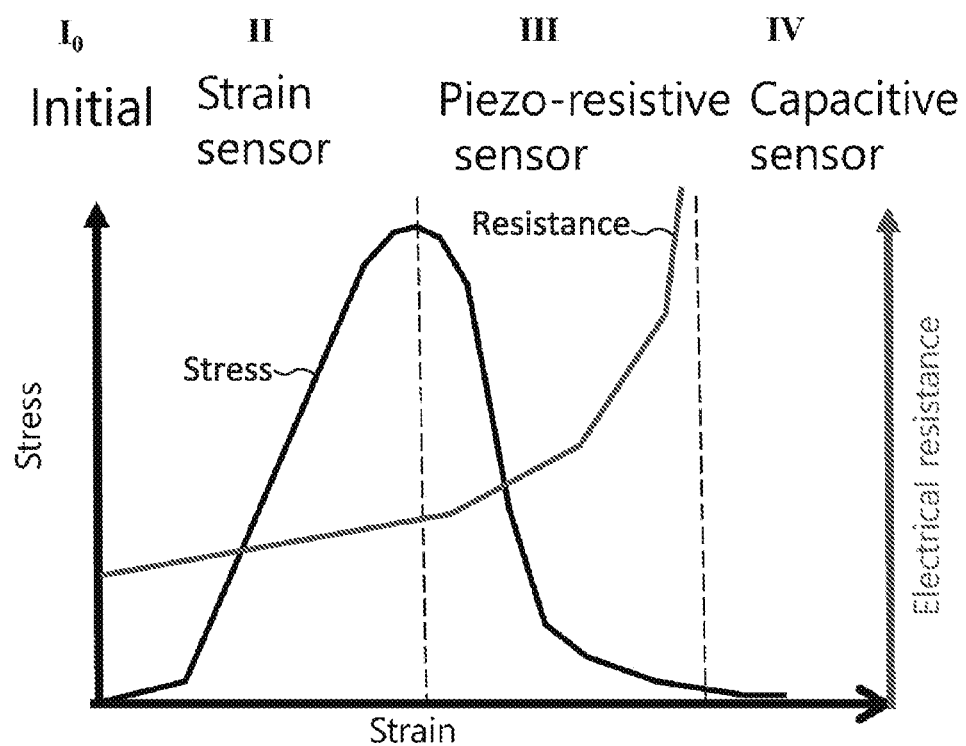

FIG. 1A shows the fabrication method of an exemplary CPC sensor. A 100 μm-thick porous paper (KimWipes®) was used as a template. An aqueous solution of multiwall carbon nanotubes (MWCNTs) (5 mg/mL; Nanostructured & Amorphous Materials, Inc., Houston, Tex.) suspended in a surfactant (sodium dodecyl sulfate; SDS; 1%) was deposited onto porous paper. When MWCNT solution was introduced to a cellulose fiber matrix, MWCNTs were bound on fibers and spanned between fibers by capillary action. Silver paste was applied to both ends of the paper strip and cured to fabricate electrodes. The composite was stretched to induce a crack due to the fracture of the tensional directional fibers. The fractured composite was attached on a double-sided adhesive tape and sealed by sticky tape to fabricate a prototype sensor.

As illustrated in FIG. 1B, the sensor can be designed and fabricated to exploit different sensing mechanisms by the magnitude of applied pre-strain, including, but not limited to the applications of: in-plane strain sensor, out-of-plane piezo-resistive sensor, and capacitive sensor in stage II, III and IV, respectively. The stress-strain relationship shows three different stages in terms of the mechanical and electrical behavior. The electrical resistance at the initial stage ($I_0$) increases linearly at the elastic region (stage II in FIG. 1B) by uni-directional strain. With the application of larger strain, a crack is initiated and propagated along the orthogonal direction to the tension, which significantly reduces the mechanical stiffness of composite (stage III in FIG. 1B). The electrical resistance increases drastically because of the fracture of MWCNT-coated cellulose fibers. Near the crack, the untangled cellulose fibers form crossbar junctions where the coated MWCNTs exhibit out-of-plane piezo-resistivity. With larger strain, the increased stress near the crack tip terminates the composite electrically (Resistance>500MΩ) (stage IV in FIG. 1b), although the composite is still connected by untangled fibers. The stress concentration of cellulose fibers along the crack edge increases the local strain and the deposited MWCNTs along the edge are disconnected. The numerous junctions create an out-of-plane piezo-capacitive sensor.

Figure 6:
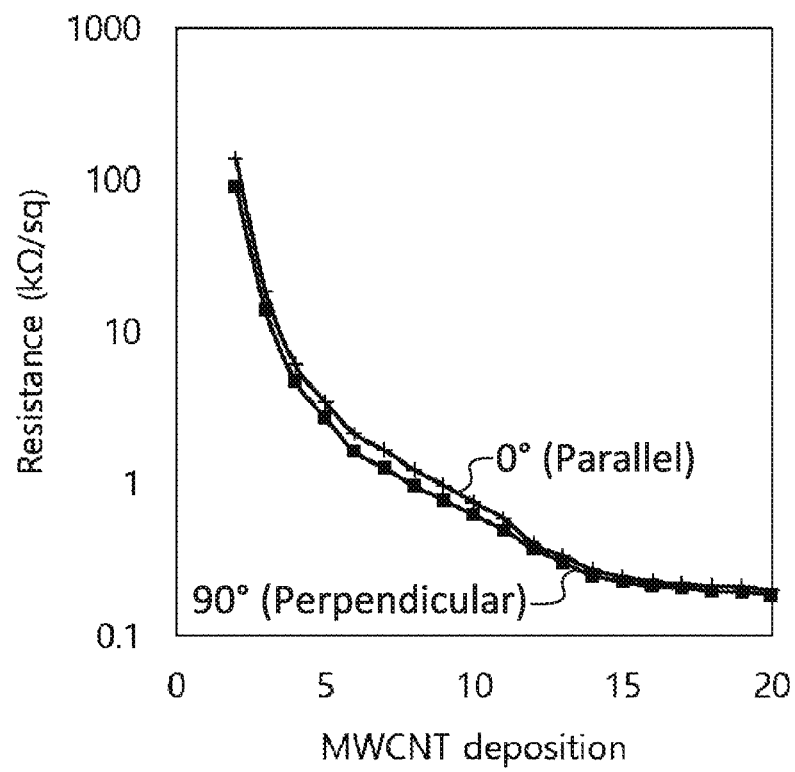
FIG. 6 shows sheet resistance of a composite for a MWCNT deposition number for both 0° and 90° directions.

In mechano-electrical characterization, the composites deposited with 0, 3, 10, and 20 times of MWCNTs were prepared to vary electrical paths. The number of depositions was limited to 20 at which the cellulose fiber matrix was fully saturated with MWCNTs. The sheet resistance of the CPC decreased as the number of MWCNT depositions increased (FIG. 6). The composite resistance in the stretching direction was slightly lower than that of the orthogonal direction. In this study, the tension direction is defined as 0° ('parallel') and the direction orthogonal to tension is 90° ('perpendicular').

Figure 1C:
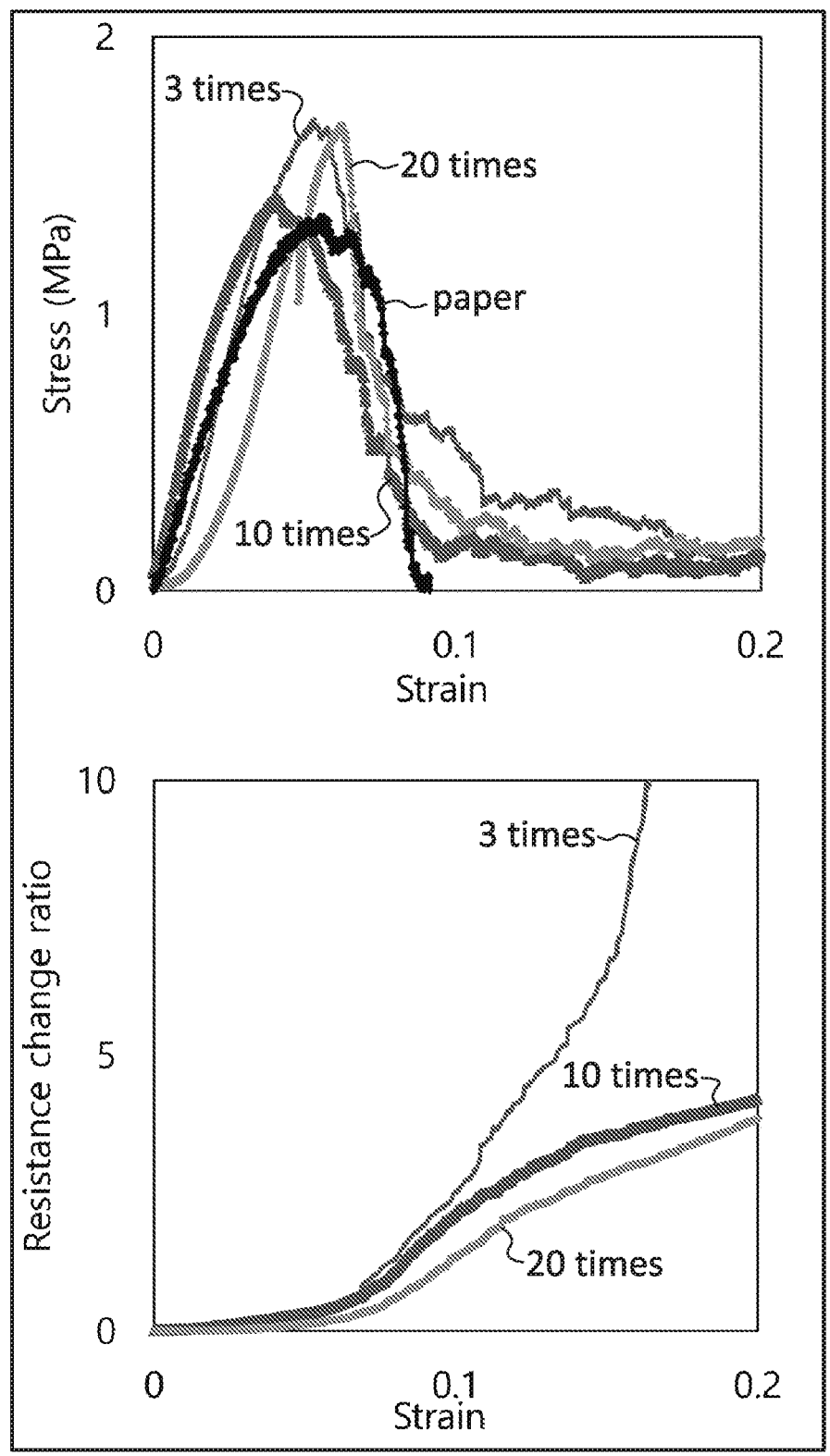
Figure 1D:
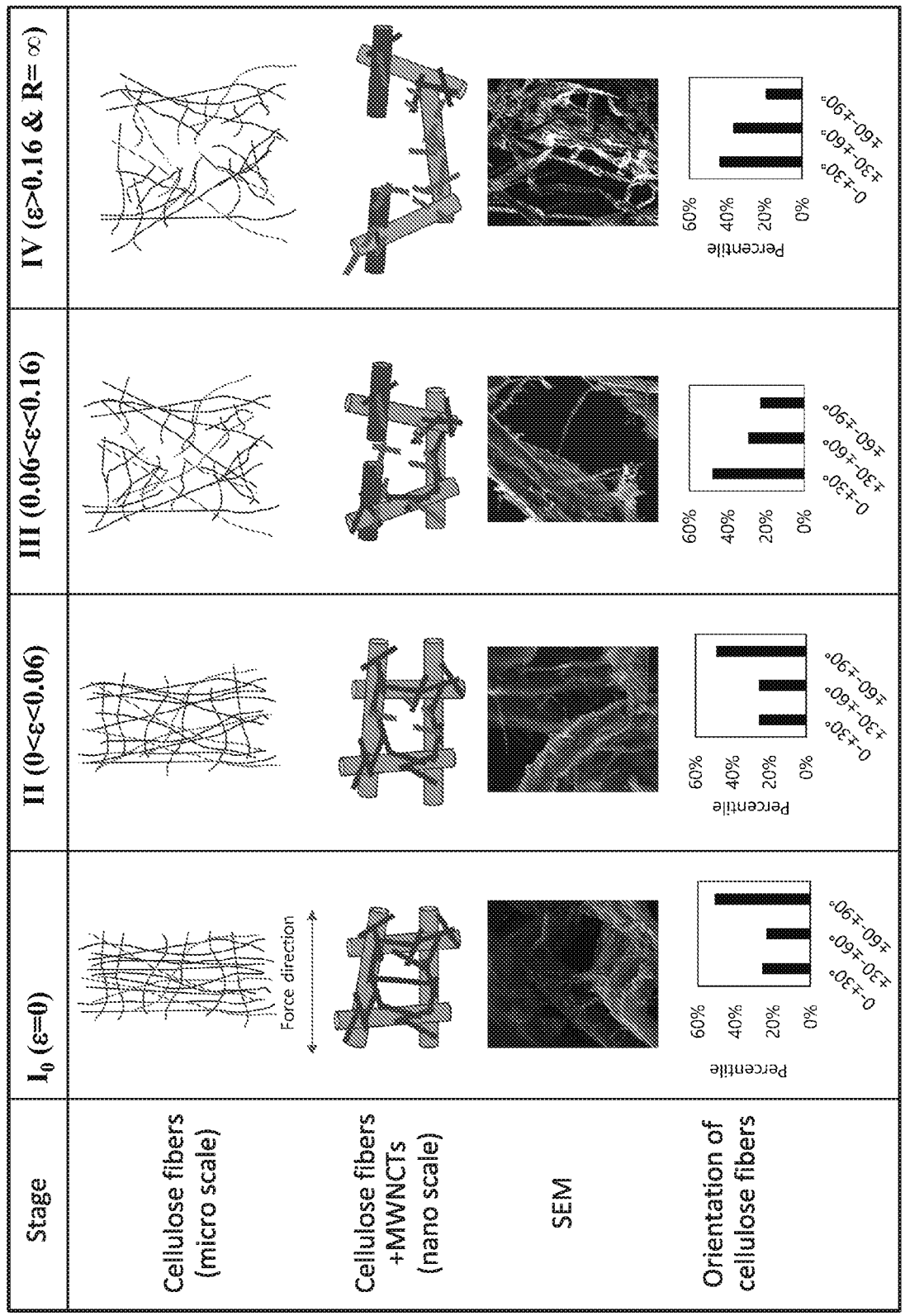
Figure 7:
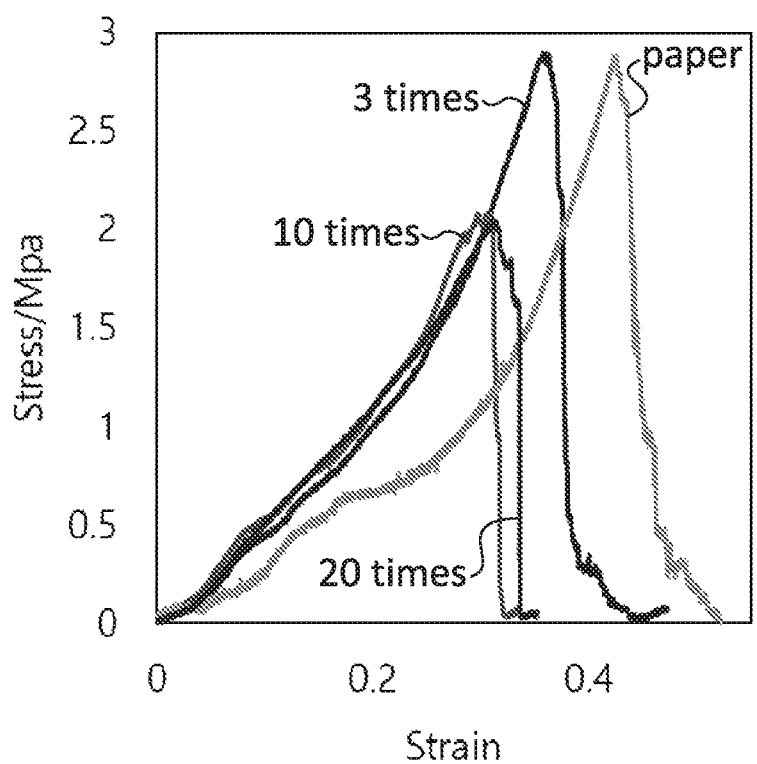
FIG. 7 shows stress-strain relationship for plain paper and CPC produced by depositing nanotubes 3, 10 and 20 times.
Figure 8:
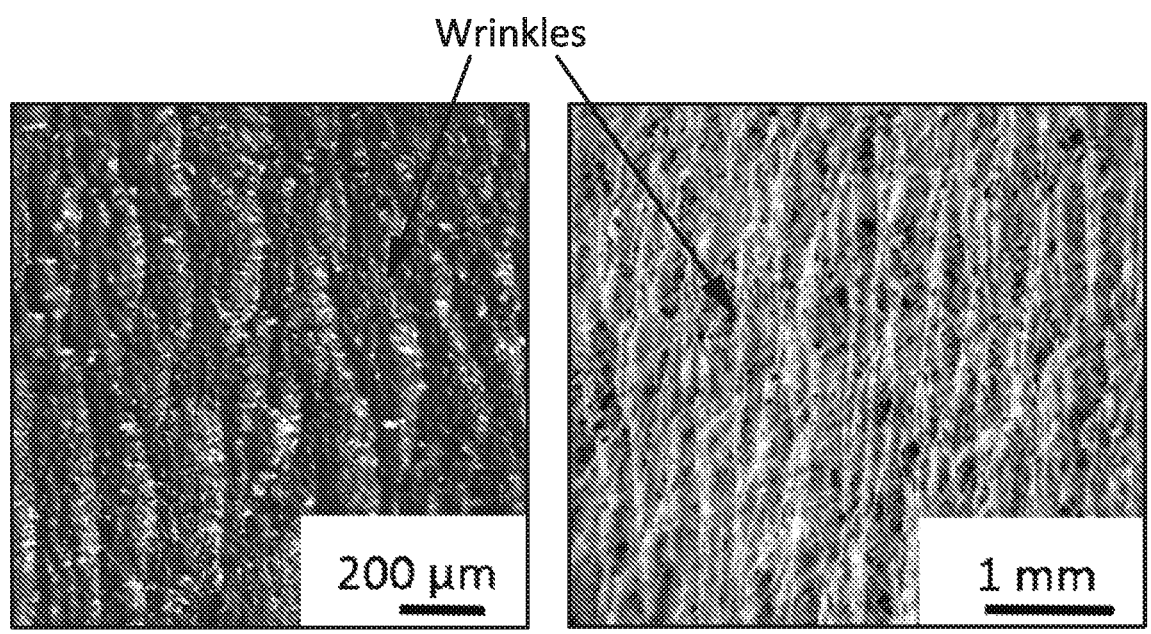
FIG. 8 shows optical microscope images of the wrinkles of the composite (3 times coated paper and plain paper).

The mechanical strength and electrical resistance change of a CPC under the uni-axial load were characterized according to the deposition numbers (FIG. 1C). The paper was composed of randomly oriented cellulose fibers as shown in the histogram of FIG. 1D. The stretching direction was perpendicular to the dominant fiber orientation at stage $I_0$. The stretching parallel to the orientation of the dominant fibers was not considered in our further test because the stress-strain relationship was not consistent (FIG. 7). The perpendicular wrinkles that were generated during the manufacturing of the tissue paper resulted in the unpredictable strain at the ultimate strength for the parallel stretching. (FIG. 8).

Figure 9:
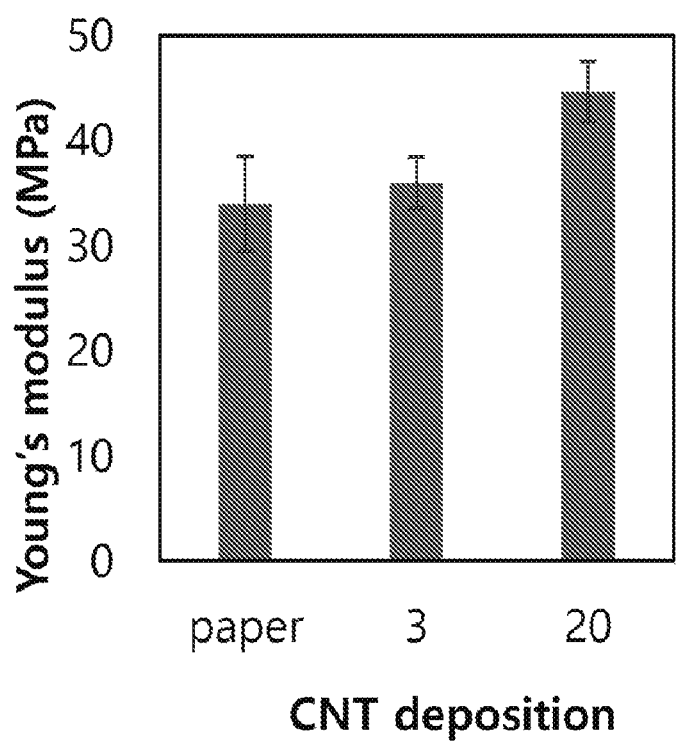
FIG. 9 is Young's modulus for plain paper and CPC produced by depositing nanotubes 3, 10 and 20 times.
Figure 10B:
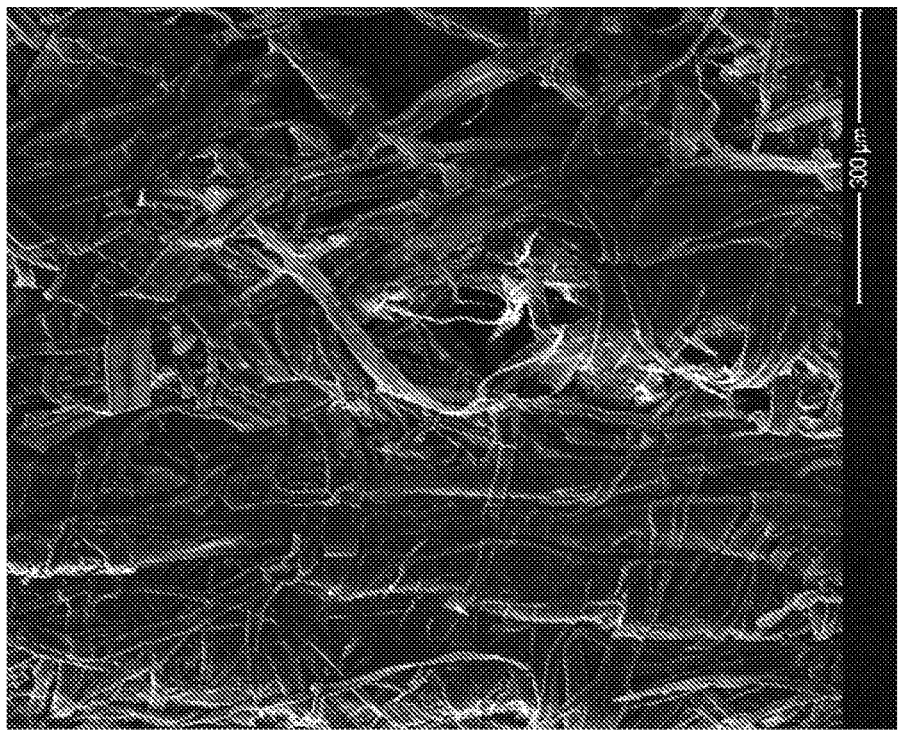
FIGS. 10A-10D are SEM images of the cellulose fibers for plain paper (10A) and CPC produced by depositing nanotubes 3 times (10B) 10 times (10C), and 20 times (10D).
Figure 10A:
Figure 10D:
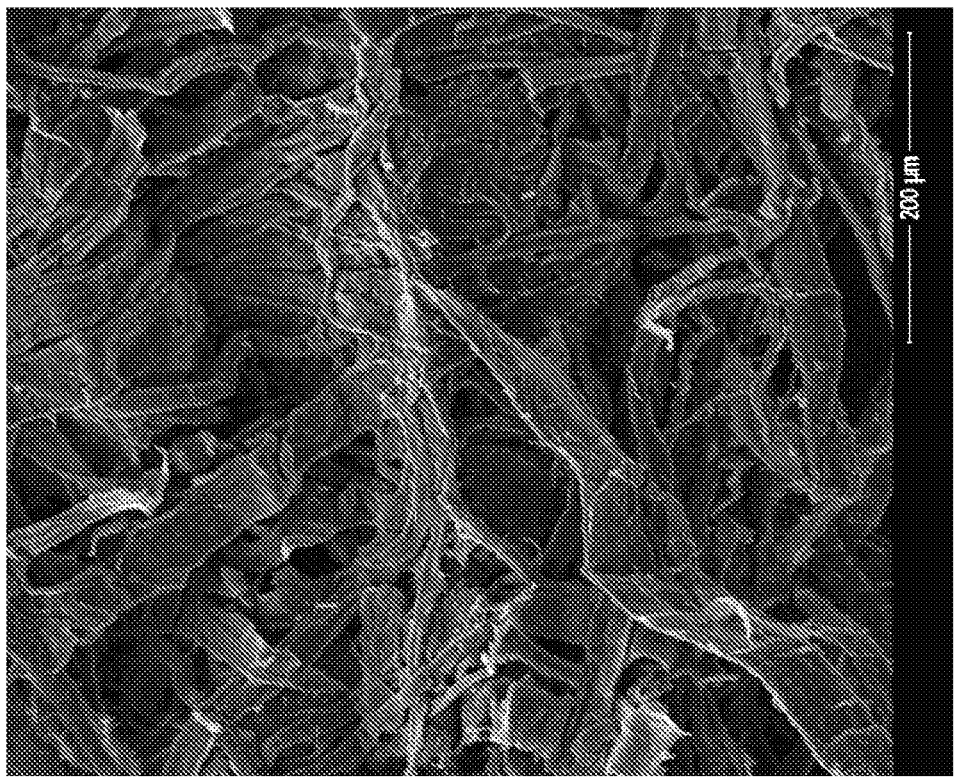
Figure 10C:
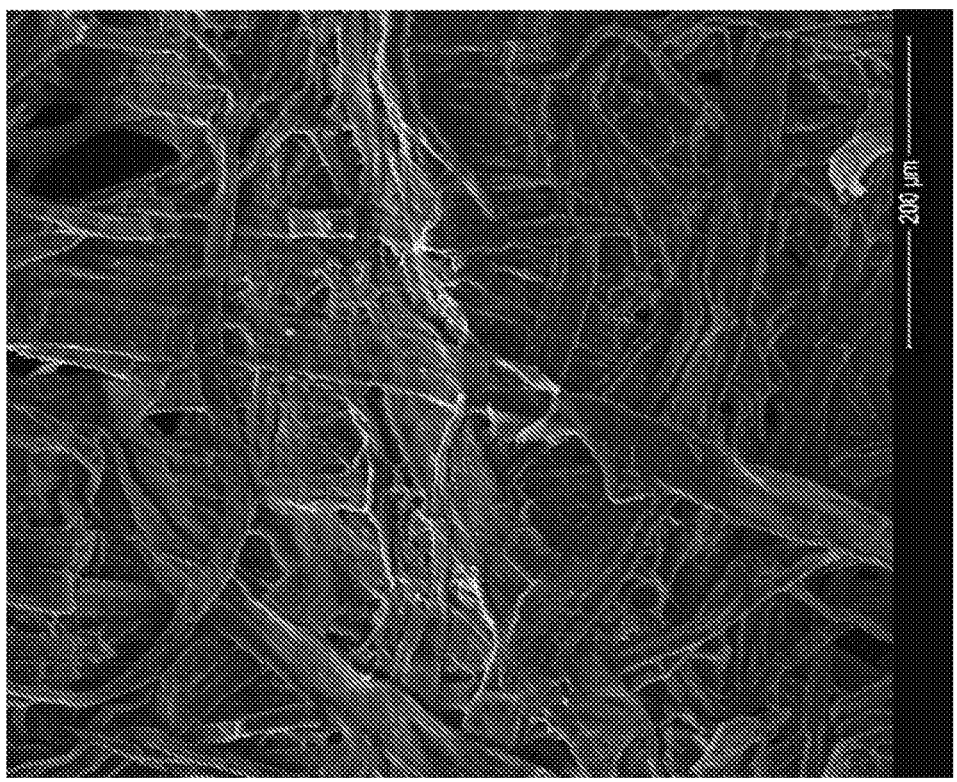

In FIG. 1C (left), regardless of the deposition numbers, the ultimate strength and its strain were in the range of 1.47±0.12 MPa and 0.053±0.0056 mm/mm, respectively. The stiffness became larger with the increase of the deposition numbers (FIG. 9). Based on the scanning electron microscopy (SEM), cellulose fibers were bridged and coated with the deposited MWCNTs (FIGS. 10A-10D), which increased the composite stiffness. When the electrical resistance was measured under tension, the inflection point of the resistance change was clearly lagged from the strain of 0.06 to 0.08 mm/mm as the deposition number increased from 3 to 20 (FIG. 1C, right). The inflection point was where the resistance change deviated the initial linear slope by 5%. As more cellulose fibers were bundled with more depositions of MWCNTs, the significantly increasing point of the resistance was delayed.

The electrical resistance increased with a power law, which agreed with percolation theory. The effective resistivity of a composite network can be expressed as $\rho_c = \rho_f (f-f^*)^{-t}$, where $\rho_f$ is the resistivity of fiber, f is the conductor volume fraction, f* is the critical conductor volume fraction, and t is an exponent. Since the fiber network in our composite is degenerated with stretching, the resistance change ratio ($R/R_0$) can be expressed with strain (ε) as $$\frac{\Delta R}{R_0} = \alpha \varepsilon^b,$$

where $R_0$ is the initial resistance, ΔR is the resistance change ($R-R_0$), and a and b are the parameters that are determined by the MWCNTs depositions. The estimated a and b for 3, 10, and 20 depositions were $1.82 \times 10^{42}$, $4.49 \times 10^4$, $1.67 \times 10^4$ and 39.0, 4.0, 4.0, respectively. The more MWCNTs were deposited, a and b were smaller because the bundled MWCNTs lagged the inflection point of the resistance change.

Figure 11:
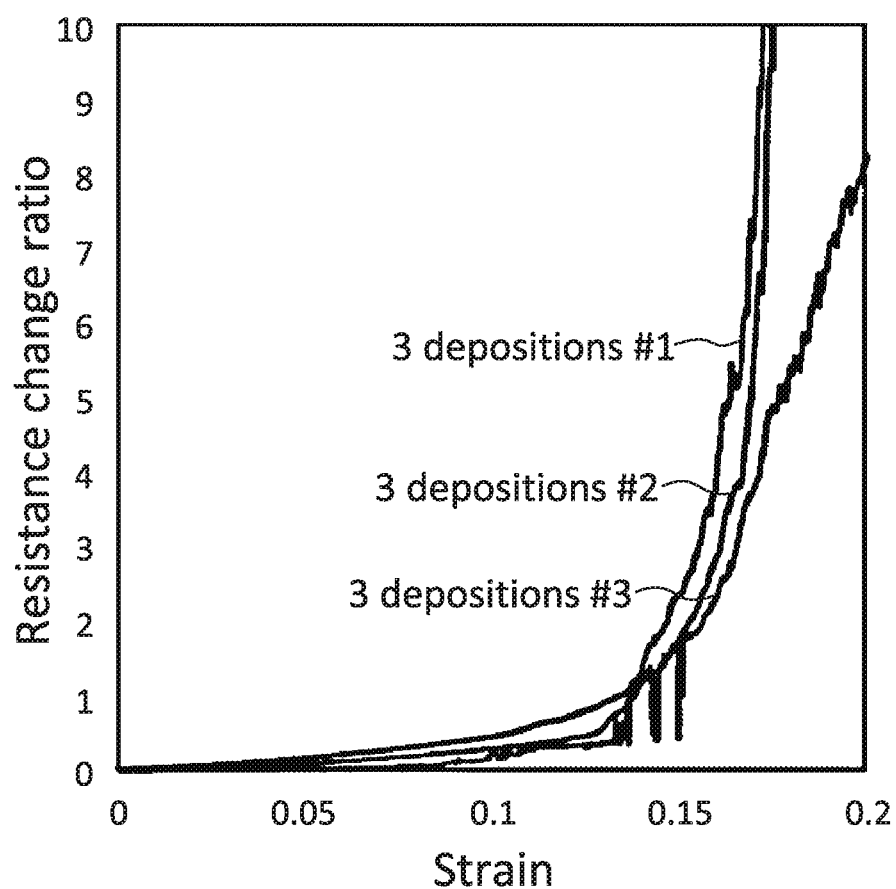
FIG. 11 shows resistance change ratio to the applied strain for the tensile test using the CPC with 3 times MWCNTs depositions.
Figures 12A, 12B, 12C, 12D:
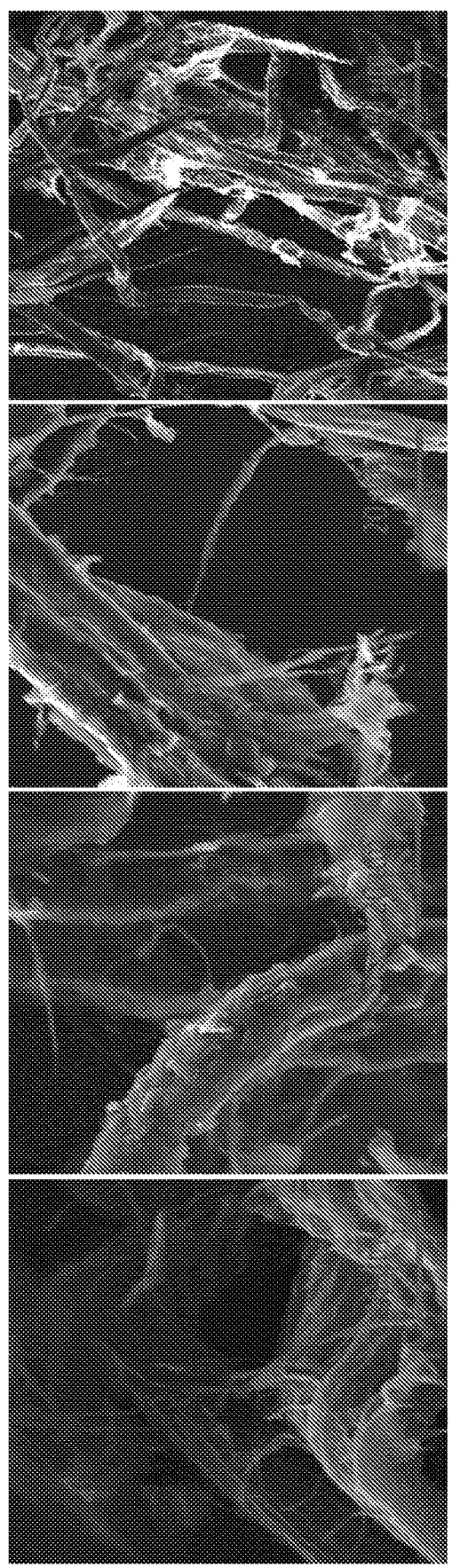
FIGS. 12A-12D show SEM images of the nanostructure of CPC coated with 3 times of MWCNTs at different strain stages. MWCNTs span and coat cellulose fibers at stage $I_0$ (12A). As the strain increases, the spanning MWCNTs are broken followed by the fracture and separation of cellulose fibers coated with MWCNTs: stage II (12B), stage III (12C), and stage IV (12D).
Figure 13:
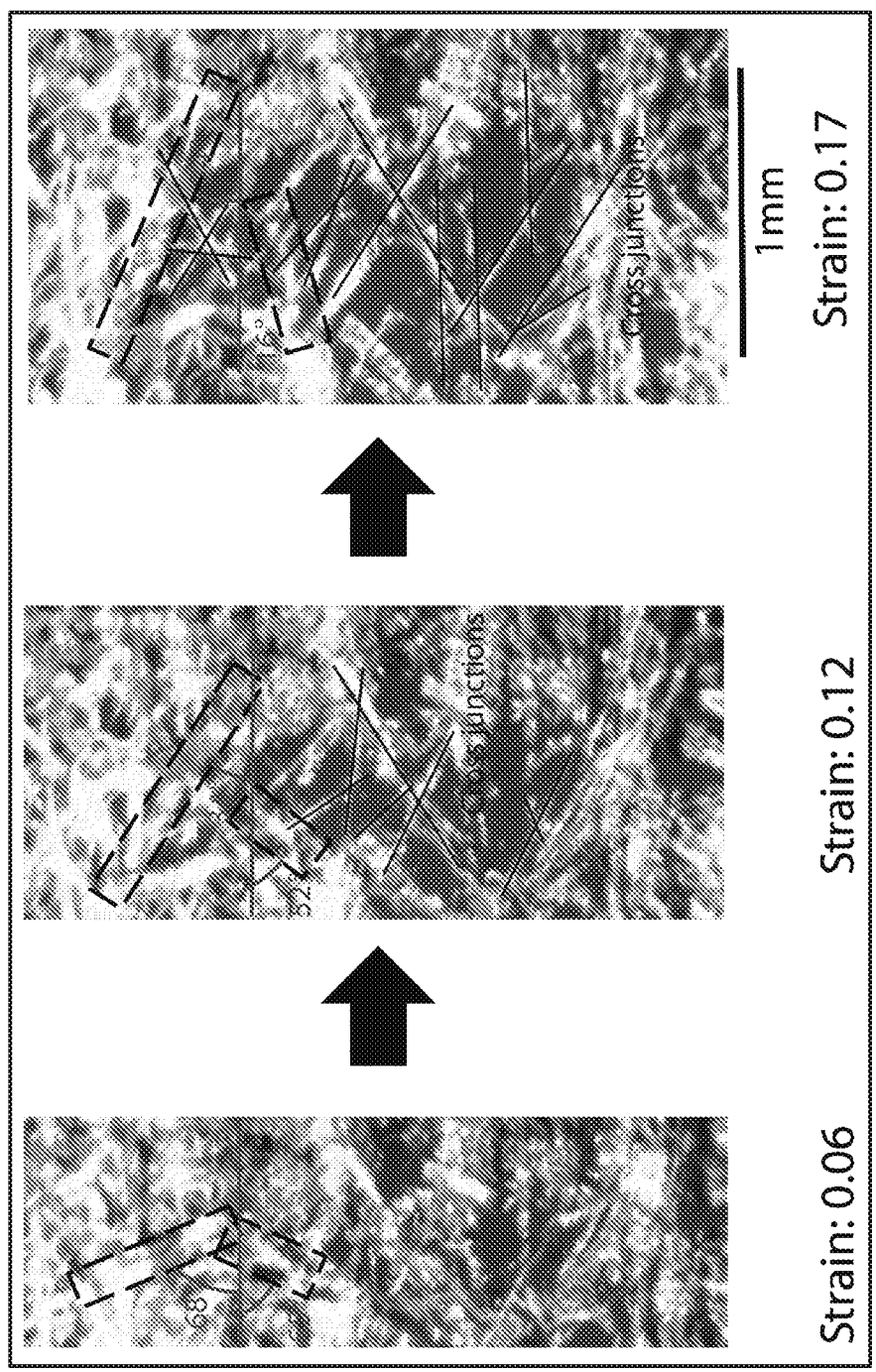
FIG. 13 shows orientation and cross junction formation of cellulose fibers according to strain.
Figure 14A:
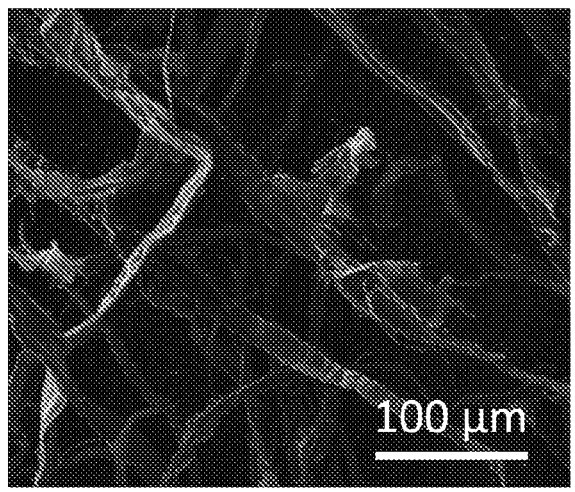
FIGS. 14A-14D are SEM images of the cross junction structure of a fractured CPC (pre-strain: 0.12) coated with MWCNTs 3 times.
Figure 14B:
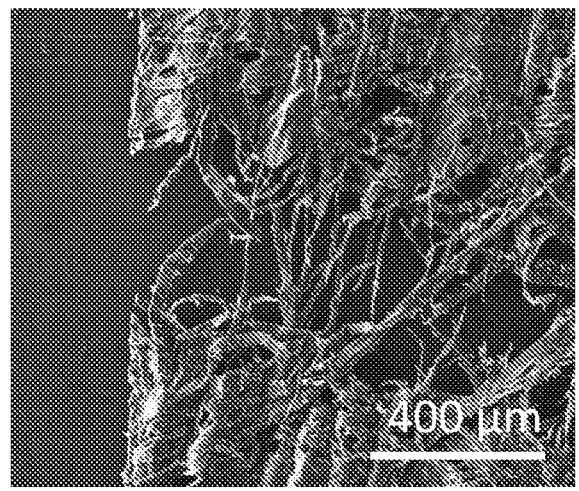
Figure 14C:
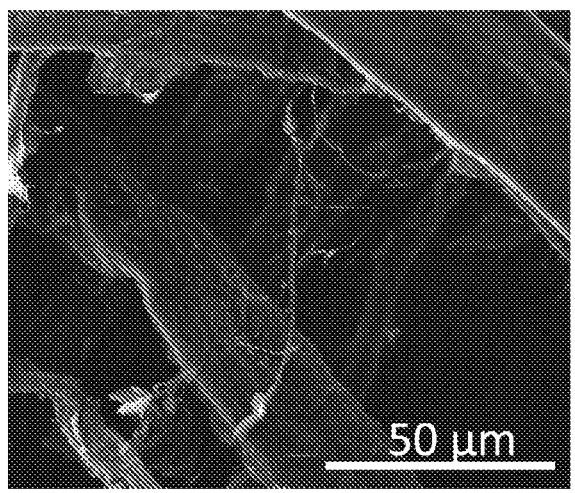
Figure 14D:
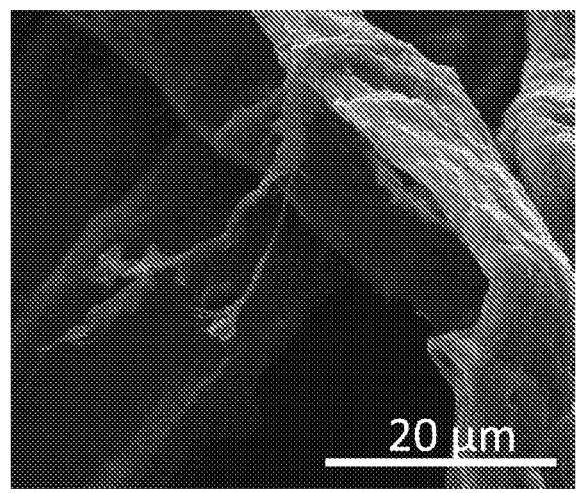
Figure 15:
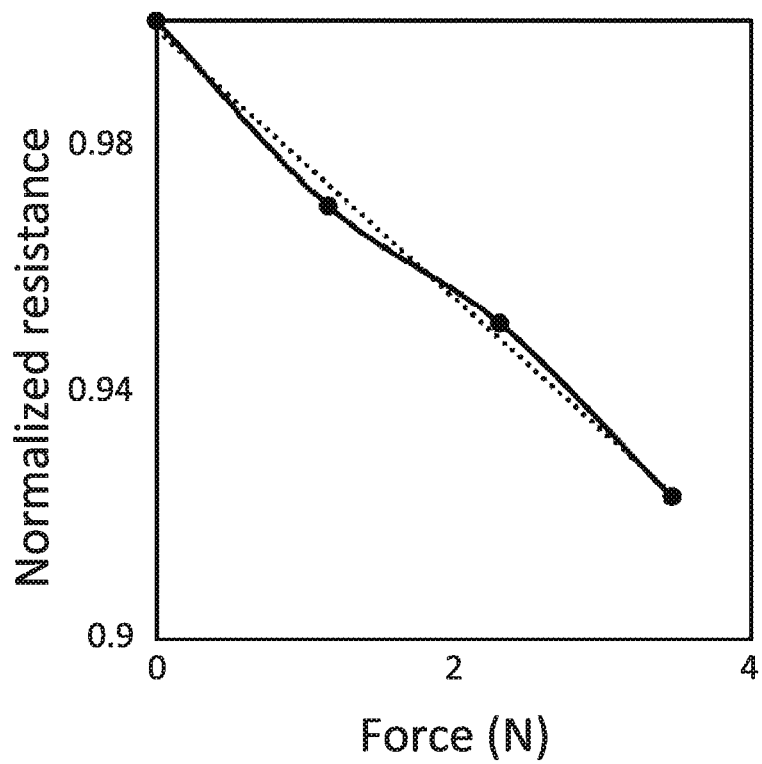
FIG. 15 shows normalized resistance change for a compressive force.
Figure 16:
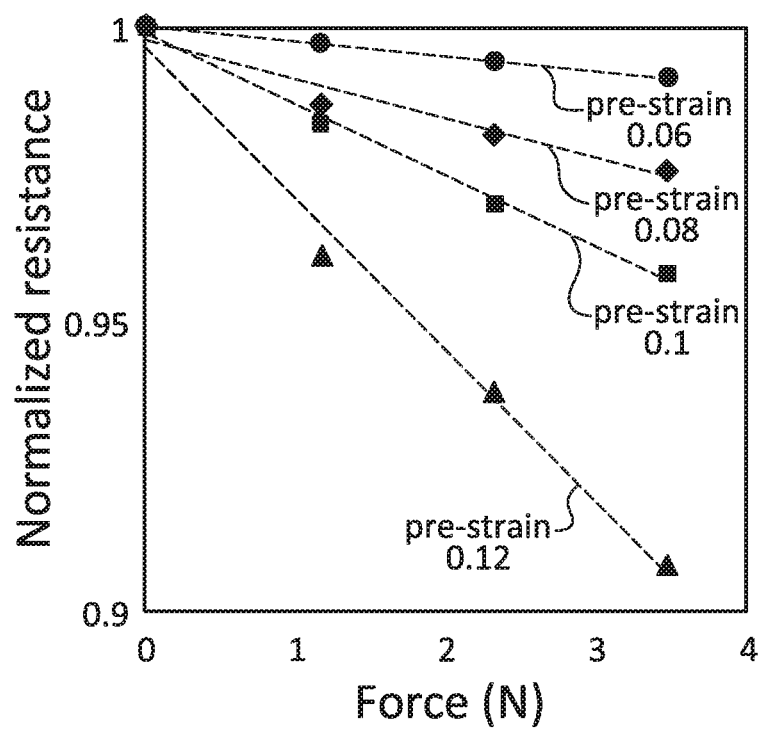
FIG. 16 shows normalized resistance change of the piezo-resistive sensors to the applied force for the sensors having the pre-strain of 0.06, 0.08, 0.10, and 0.12.

FIG. 1D shows the structural change of the cellulose fibers and MWCNTs under tension based on optical and SEM study. A CPC with 3 times MWCNT depositions was used for this study. The resistance change for 3 times-MWCNT deposited CPC during the tensile test was relatively uniform as shown in FIG. 11. The creation of piezo-sensitivity stems from the realignment and fracture of CPC network under tensile loading. The bottom graphs of FIG. 1D show the percentile histogram of the fiber orientations in stage of $I_0$, II, III, and IV. According to the SEM observations, the fiber orientations in the area of 1×1 mm² were divided into three ranges of 0~±30°, ±30~±60°, and ±60~±90°. In the original paper template (stage $I_0$), 26% of the fibers were in 0~±30°, 23% in ±30~±60°, and 51% in ±60~±90°. Therefore, the dominant orientation in the initial composite was ±60~±90°. Here 0° and 90° imply parallel and perpendicular directions to the loading.

In stage II (0<ε≤0.06), the parallel fibers were straightened and stiffened by tension. The resistance increase was resulted from the breakage of the MWCNT bridges spanning neighboring cellulose fibers. Although a CPC was stretched in an elastic range, the resistance was not recovered to the original value due to the broken MWCNT bridges (FIGS. 12A-12D).

In the strain of 0.06~0.16 (stage III), most parallel fibers were fractured at ultimate strength. Both inclined and perpendicular fibers were oriented to the tensile direction, which changed the dominant orientation of fibers into ±0~±30° (shown on the histogram in FIGS. 1D and 13). Both spanning and coated MWCNTs on fibers were broken. The reorganized fibers (FIG. 1D) formed numerous cross-shaped junctions (FIGS. 14A-14D). Electrical resistance was significantly increased as the MWCNT network among the fractured fibers was broken.

Although cellulose fibers were deformed, buckled, and fractured in the stage, MWCNTs were not delaminated or separated from the fibers. According to our SEM study, the diameter of the cellulose fibers ranged from 10 to 30 μm, and the curvature radius of the cellulose fibers was larger than one hundred micrometers. The diameter and the length of the MWCNTs were 8~15 nm and 0.5~2 μm, respectively. Compared with the MWCNT dimensions, the fiber dimensions were significantly larger than the cellulose fibers. In CPC, MWCNTs were tightly bonded on cellulose fibers by hydrogen-, ionic- and nonspecific bondings in conjunction with capillary action in the deposition process.

At the stage where the strain was greater than 0.16 (stage IV), all the electrical connections were broken by extreme stretching. The composite was electrically terminated along the crack edge, which was clearly observed from the bright and dark contrast in the SEM image (FIG. 1D). The high contrast indicated that electrons could not flow through the crack edge. In the orientation graph, the fraction of the parallel and inclined fibers (0~±30° and ±30~±60°) became 80%, forming crossbar junctions. Since the resistance became infinite, pure capacitance of the MWCNTs could be measured through the dielectric media of air and fibers.

By the control over the applied strain to the CPC, at least the following different sensors: a strain sensor, a piezo-resistive sensor, and a piezo-capacitive sensor can be designed in the stages II, III, and IV, with strongest results expected for those sensors in those stages respectively. To demonstrate this, a series of prototypes were fabricated in stages II~IV. The CPC pre-strained at the stage II by applying 0, 0.02, 0.04 and 0.06 of strains was prepared and attached to a polydimethylsiloxane (PDMS) cantilever beam for the sensor evaluation (FIG. 2A). With the bending of the cantilever, the top surface of the beam was stretched, which linearly increased the sensor resistance (FIG. 2B). As the pre-strain increased from 0 to 0.06, a gauge factor $$\Delta R \left( \frac{R_0}{\Delta \varepsilon} \right)$$

increased from 2 to 13 (FIG. 2C). The operation range of the strain sensor was below 0.01. If the applied strain exceeded 0.01, the gauge factor could be changed as tested. The initial resistances of the four specimens at the strains of 0, 0.02, 0.04 and 0.06 were 83, 87, 93 and 100 k$\Omega$, respectively. The increase of the gauge factor in the elastic region was caused by the breakage of the MWCNT bridges among the intact cellulose fibers. Therefore, a pre-strain could partially remove the electron paths spanning cellulose fibers, which increased the sensitivity.

In stage III, the reoriented cellulose fibers in the crack generated sensitivity for out-of-plane directional force. The sensing performance was evaluated by recording the electrical resistance change with respect to the applied force. An elastomeric finger was fabricated using PDMS to mimic a human finger (FIG. 3A). To calibrate the applied force, a force sensor (LCFD1KG, Omega Engineering, Norwalk, Conn.) was attached under the sensor substrate. As the force was applied on the cracked area of the composite, the untangled crossed fibers generated in the fracture were compressed to increase the contact area, which decreased the resistance in proportion to the force (FIG. S10, Supporting information).

The piezo-resistive sensitivity was defined as $$\frac{\Delta R / R_0}{\Delta F},$$

where $\Delta R$ was the resistance change of the sensor, $R_0$ was the initial resistance of the sensor, and $\Delta F$ was the change of the applied force. The sensitivity was increased by larger pre-strain (FIG. 3B). As the pre-strain increased from 0.06 to 0.13, the sensitivity rapidly increased from 0.002 to 0.023 N$^{-1}$. The response of the resistance change to the applied force for the 3 times-MWCNT deposited CPC is shown for the pre-strain of 0.06, 0.08, 0.10 and 0.12 (FIG. S11, Supporting information). Without the pre-strain, the piezo-sensitivity was close to 0 because the cellulose fibers were firmly bonded with numerous MWCNT network. To validate if the sensitivity was created by a crack, the forcing point was moved from a crack tip (0 mm) to 8 mm by a 2 mm-step along the longitudinal direction. The sensitivity was continuously reduced from 0.022 to 0.001 N$^{-1}$ as the distance (d in FIG. 3C) from the crack tip increased (FIG. 3C). When the distance from the crack was greater than 8 mm, the composite was not sensitive to an out-of-plane force. To test the reproducibility and the MWCNT deposition effect, the composites deposited with 3, 10 and 20 times were stretched by pre-strain of 0.12 mm/mm. The sensitivity was reduced as the deposition numbers increased because more bundled fibers by MWCNTs limited the structural change under tension (FIG. 3D). With more depositions, fewer junctions were created to lag the increase of the resistance, thus the sensitivity.

Figure 17:
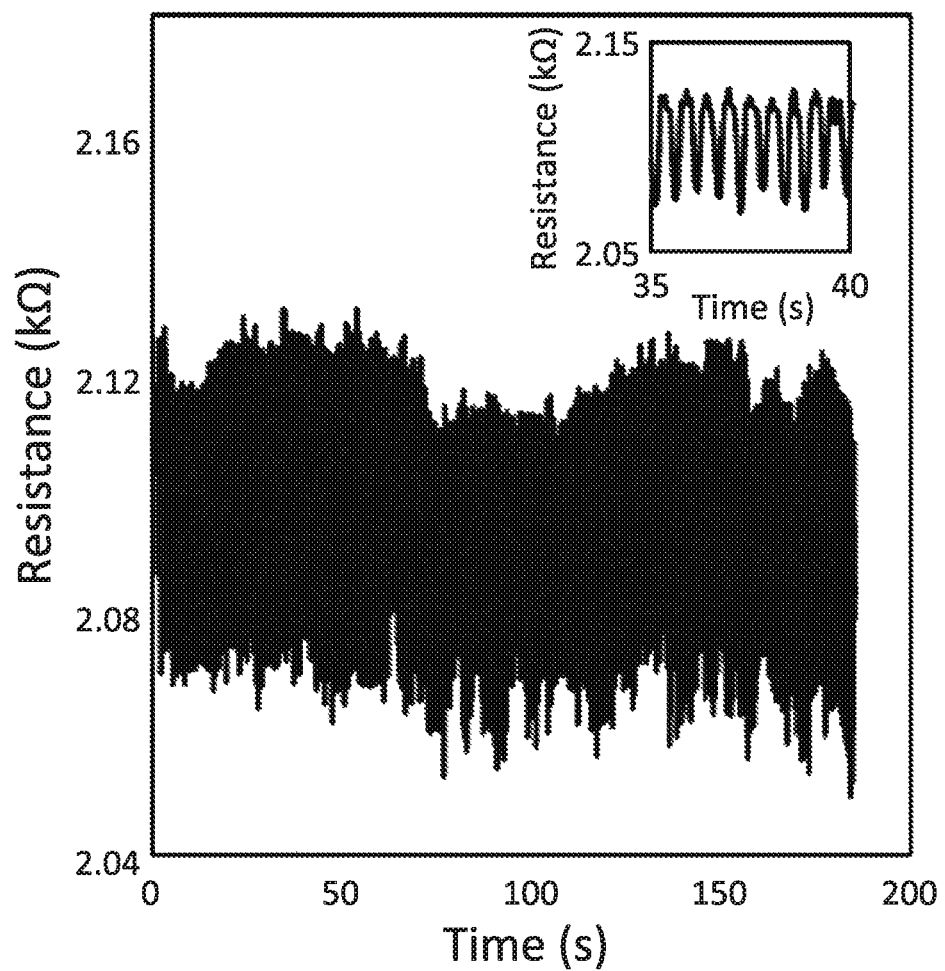
FIG. 17 shows resistance change for a cyclic finger force on the sensor.

When a step force input was applied to a composite with a 0.12-prestrain, the response time was less than 50 ms, which was significantly smaller than other polymer sensors (FIG. 3E). However, the resistance offset was continuously reduced for 100 seconds. Under the force, the cellulose fibers continuously slipped and creeped, which caused the continuous decrease of the resistance. When a cyclic loading (frequency: 0.3 Hz) was applied between 0 to 5.5 N, the resistance changed periodically, and the resistance offset reached a steady state after 300 s (FIG. 3F). The response of the sensor pressed by a human finger was relatively reliable for 500 cycles (FIG. 17).

Figure 4A:
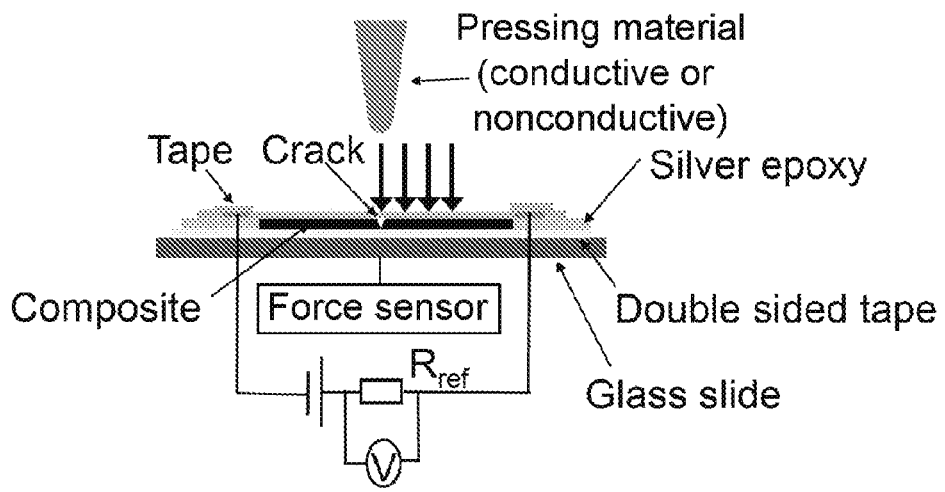
FIGS. 4A-4F illustrate evaluation of an exemplary capacitive sensor in stage IV.

In stage IV, a capacitive sensor is created. Since the final fracture of the composite was not predictable, the applied pre-strain was stopped when the resistance became larger than 500 M$\Omega$. Similar to the piezo-resistive sensor, junctions were created by the crossed structure of cellulose fibers. Due to the large surface areas of cellulose fibers and MWCNTs, intrinsic capacitance without parasitic capacitance was as large as 0.5±0.04 pF (N=6). The capacitance sensor could detect conductive objects by contact and non-contact modes, and non-conductive objects by a contact mode using the setup in FIG. 4A. Note that the composites deposited with 10 and 20 times MWCNTs could not be used to create a capacitive sensor because the bundled fibers by MWCNTs made the CPC electrically conductive until complete fracture.

Figure 4B:
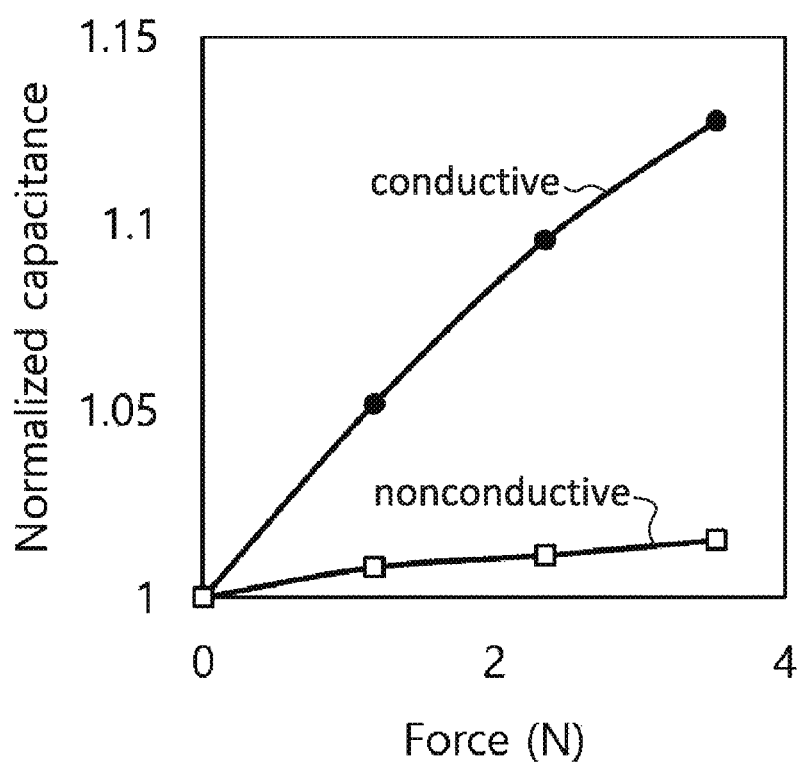
Figure 4C:
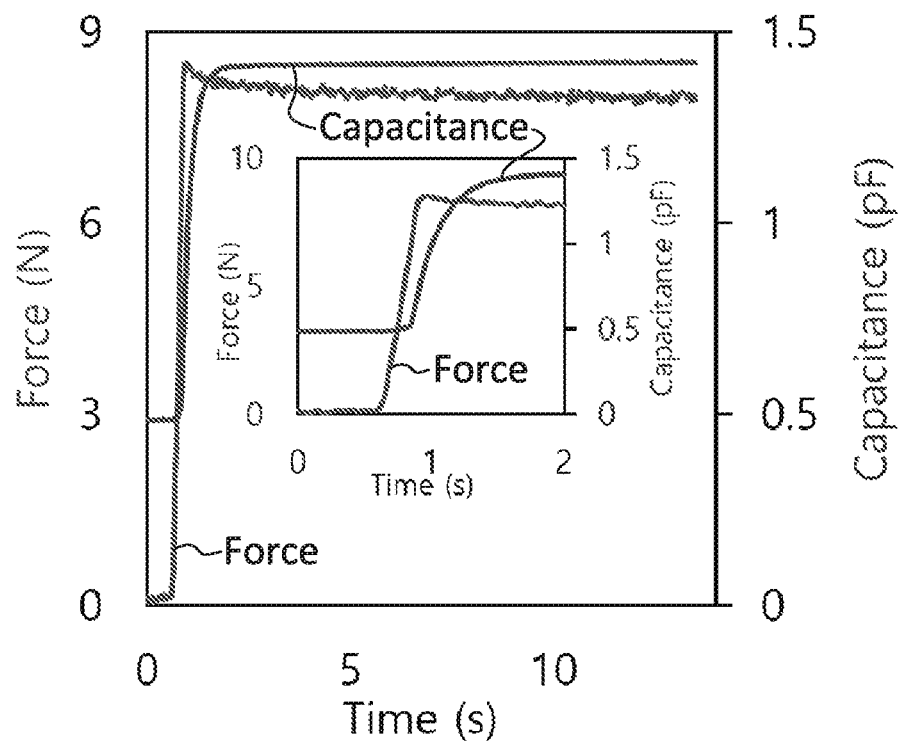
Figure 4D:
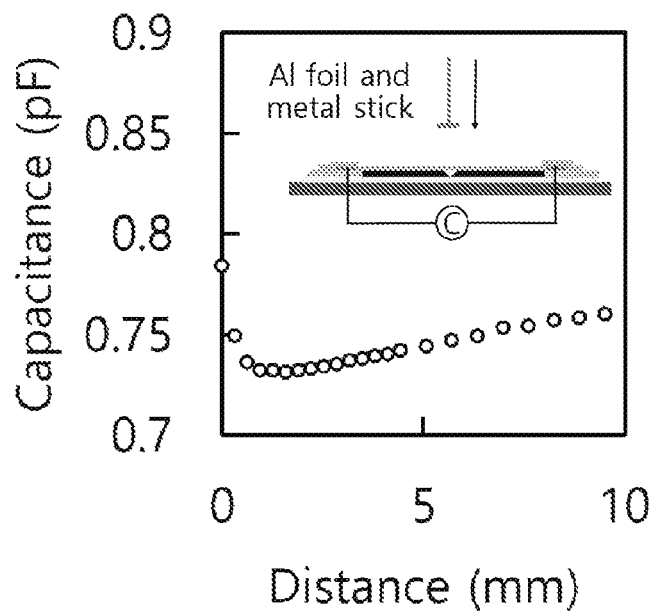
Figure 4E:
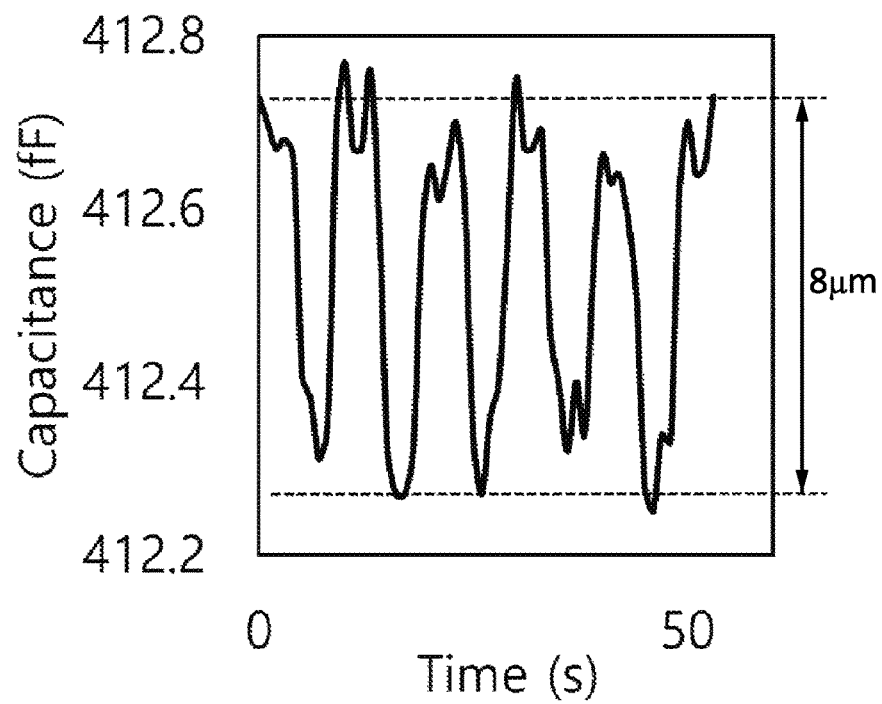
Figure 4F:
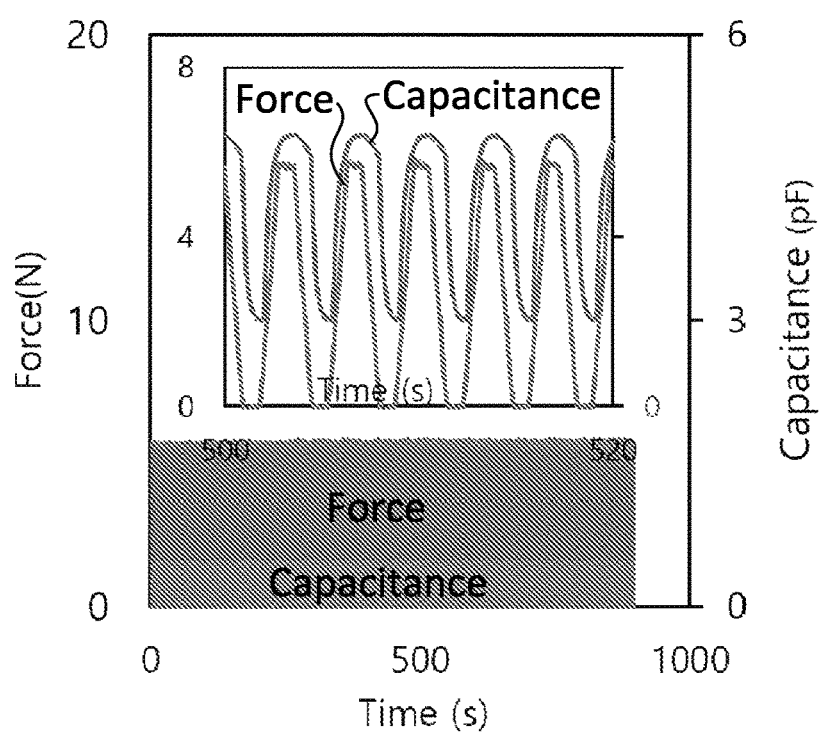

When a conductive finger (PDMS finger coated with aluminum) was forced on a crack, the capacitance increased with a sensitivity of 0.036 N$^{-1}$ (FIG. 4B). The sensitivity of a piezo-capacitive sensor was $$\frac{\Delta C / C_0}{\Delta F},$$

where $\Delta L$ was the resistance change of the sensor, and $C_0$ was the initial resistance of the sensor. The sensitivity for the same test using a non-conductive finger was reduced to 0.004 N$^{-1}$. When a step input was applied, the time constant was less than 50 ms (FIG. 4C). For the non-contact sensing mode, when a conductive object was withdrawn from the crack surface of the capacitive sensor, the capacitance was first rapidly reduced by the decrease of parallel capacitance (sensitivity: −0.068 mm$^{-1}$), and subsequently, increased by the reduction of charge dissipation (sensitivity: 0.0048 mm$^{-1}$) (FIG. 4D). Here, the sensitivity for the non-contact distance sensor was $$\frac{\Delta C / C_0}{\Delta D},$$

where $\Delta D$ was the distance change between the sensor and the object surface. For the capacitance increase, the characteristic length between the sensor and the conductor became greater than that of the capacitance sensor, which increased the capacitance by decreasing the current dissipation to the conductor. At the −0.068 mm$^{-1}$-sensitivity region, the 8 μm-displacement of a piezo-actuator could be measured (FIG. 4E). Considering the noise level, the detection limit was 1 μm. Note that the capacitance change could not be measured when a conductive object was approached to a non-cracked area. In a cyclic compressive loading of 0~5.7 N at 0.3 Hz, the sensor response was stably measured using a conductive elastomeric finger (FIG. 4F). The capacitance changed between 0.5 and 1.5 pF, which was larger than the intrinsic capacitance due to the parasitic capacitance by the wire harness. In the setup, the parasitic capacitance was 0.2 pF.

Figure 5A:
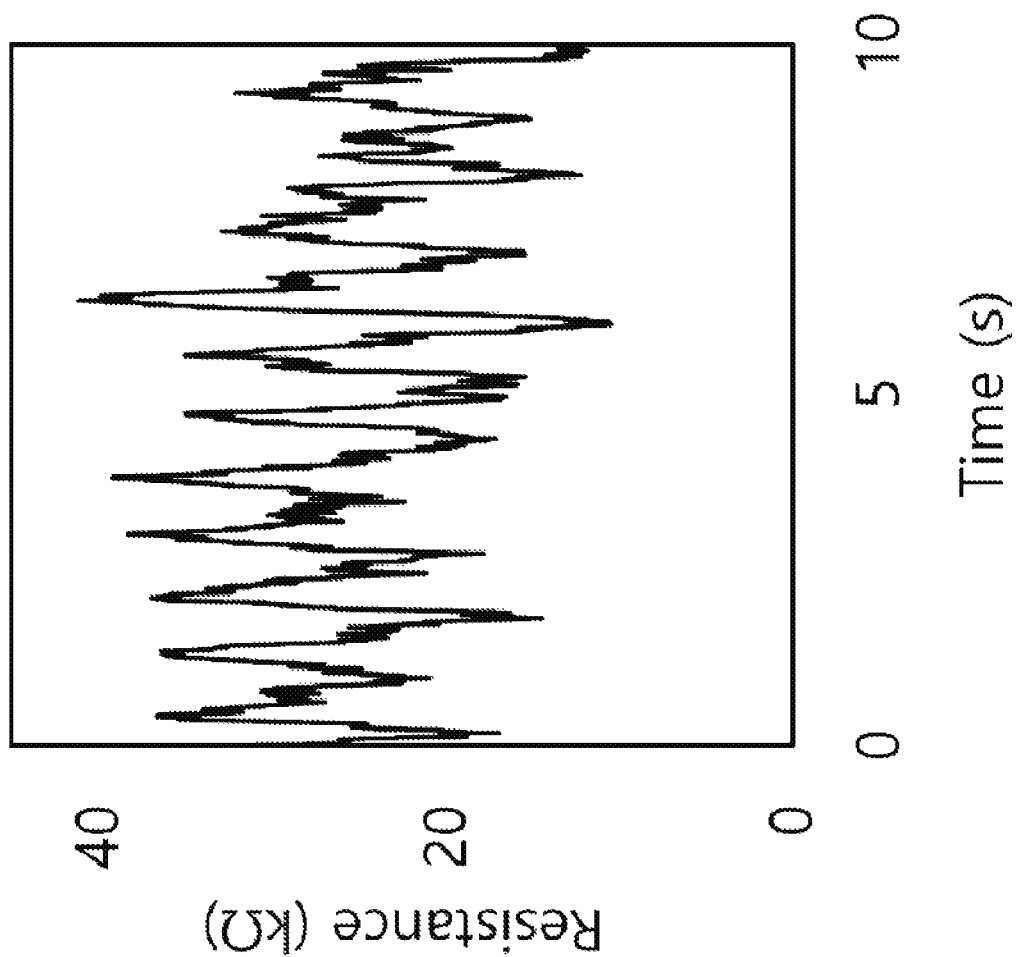
FIGS. 5A-5F demonstrate human behavior monitoring using exemplary sensors.
Figure 5A:
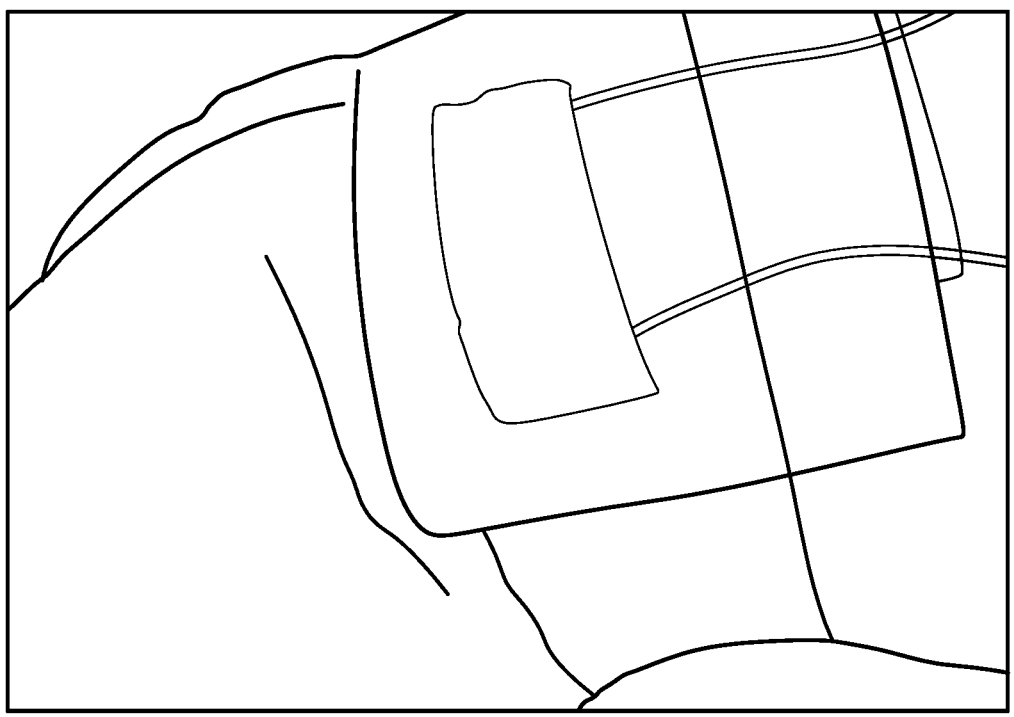
Figure 5B:
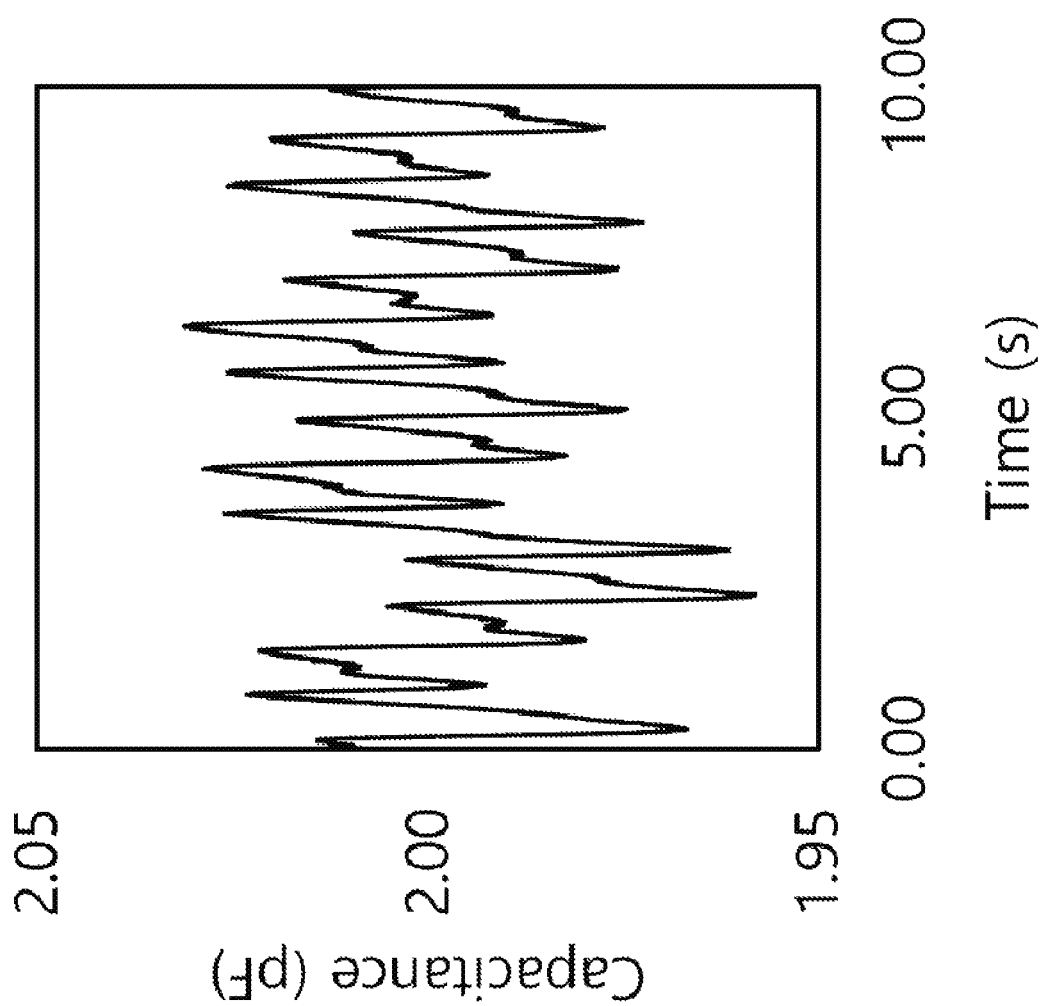
Figure 5B:
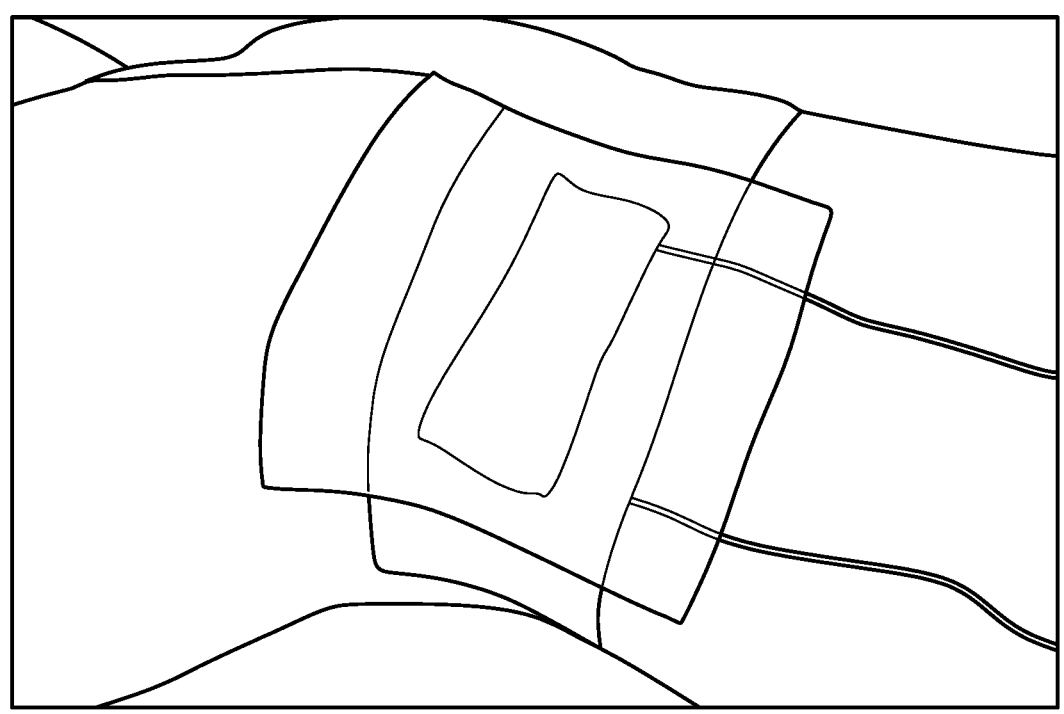

Using resistive and capacitive sensors, human behaviors can be monitored. Both sensors can be used to measure heartbeats on wrist (FIGS. 5A and 5B). The offset change of the heartbeat signal might be generated from the cardiac impulse during the heartbeat. In comparison to other results, the offset fluctuation was in an acceptable range. In the measurement, a CPC sensor on a both-side sticky tape was attached on the wrist.

Figure 5C:
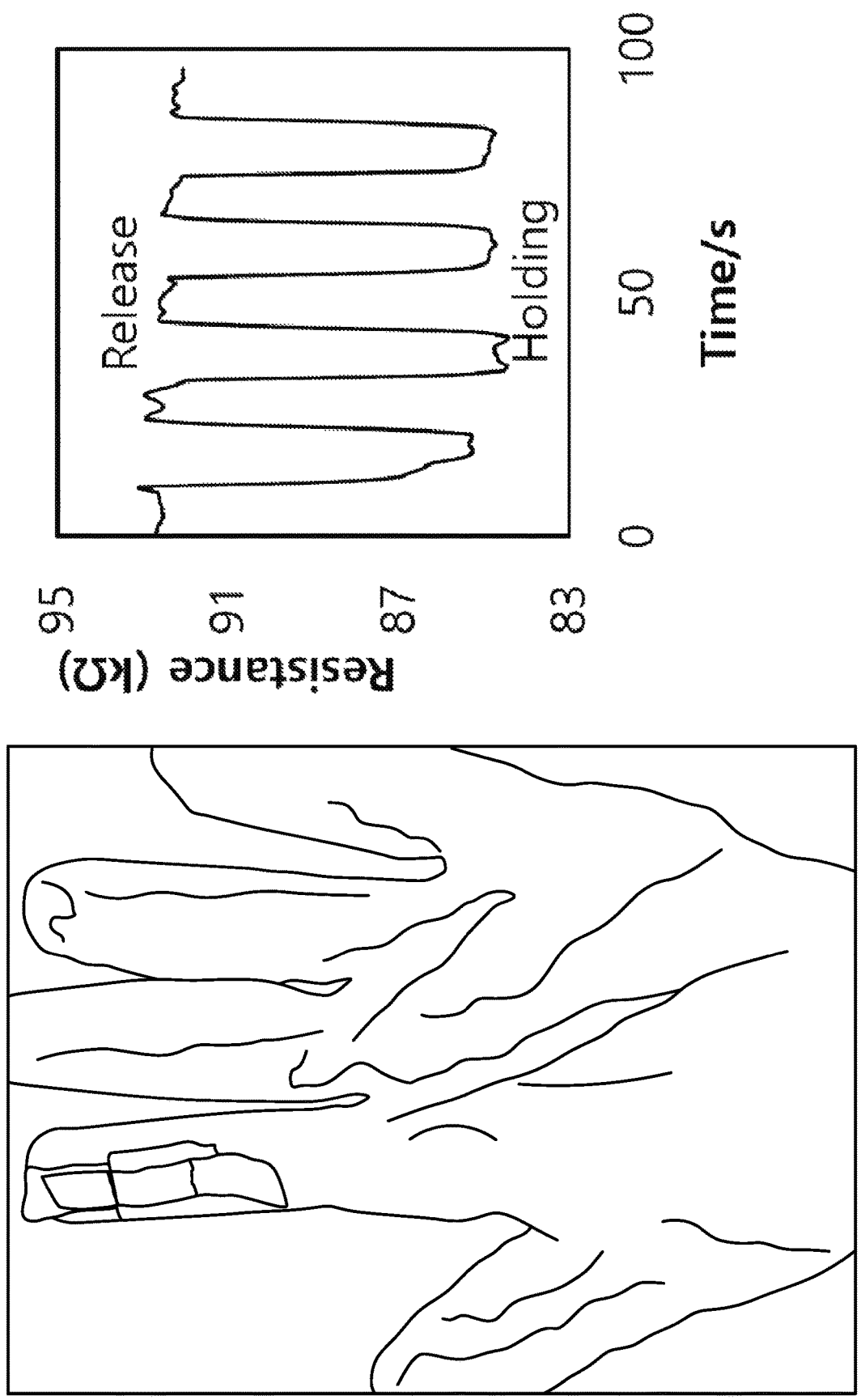
Figure 5D:
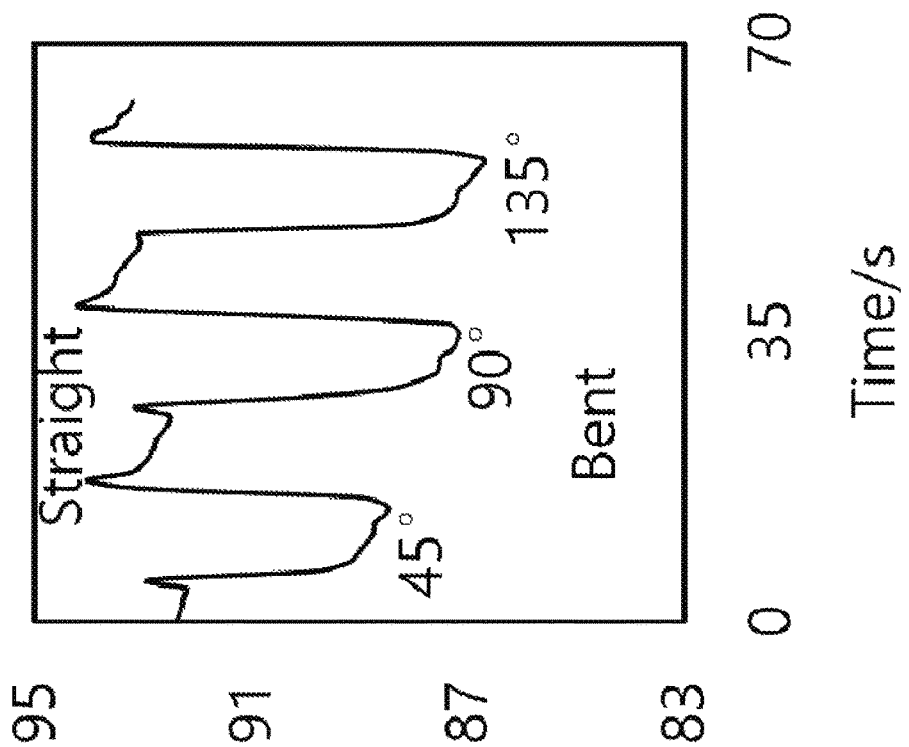
Figure 5D:
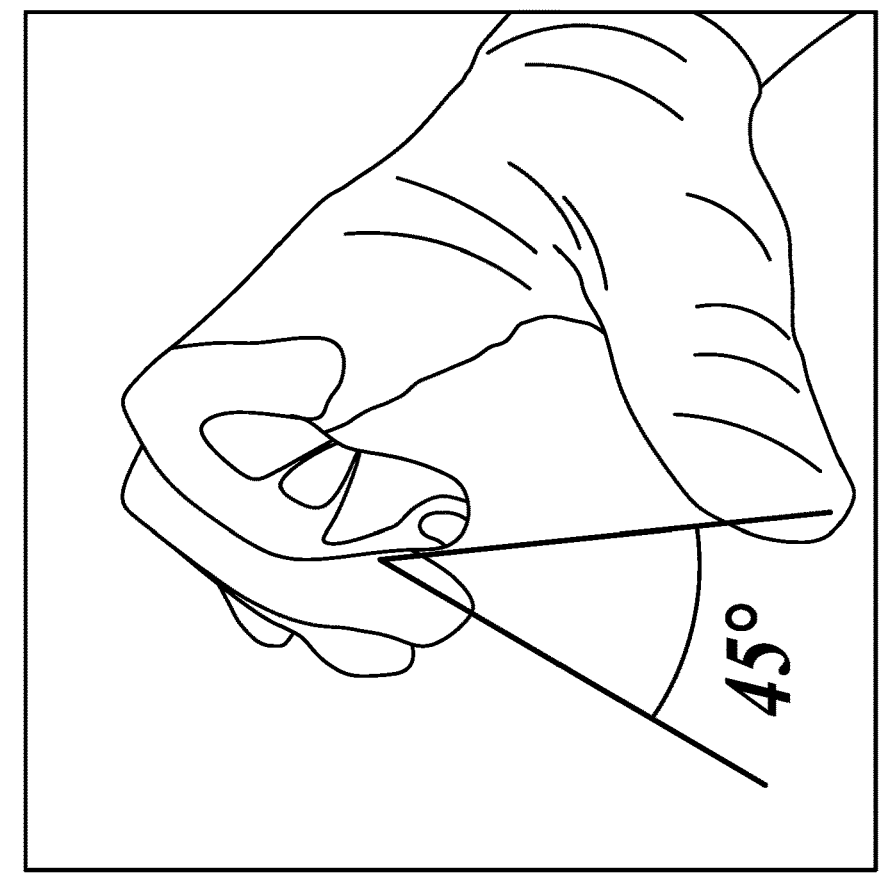

When a piezo-resistive sensor was attached on a finger of a glove, cyclic gripping motion can be detected (FIG. 5C). When a sensor was attached on a finger joint, the resistance change can be measured for the angle change between 0 and 135 degrees (FIG. 5D).

Figure 5E:
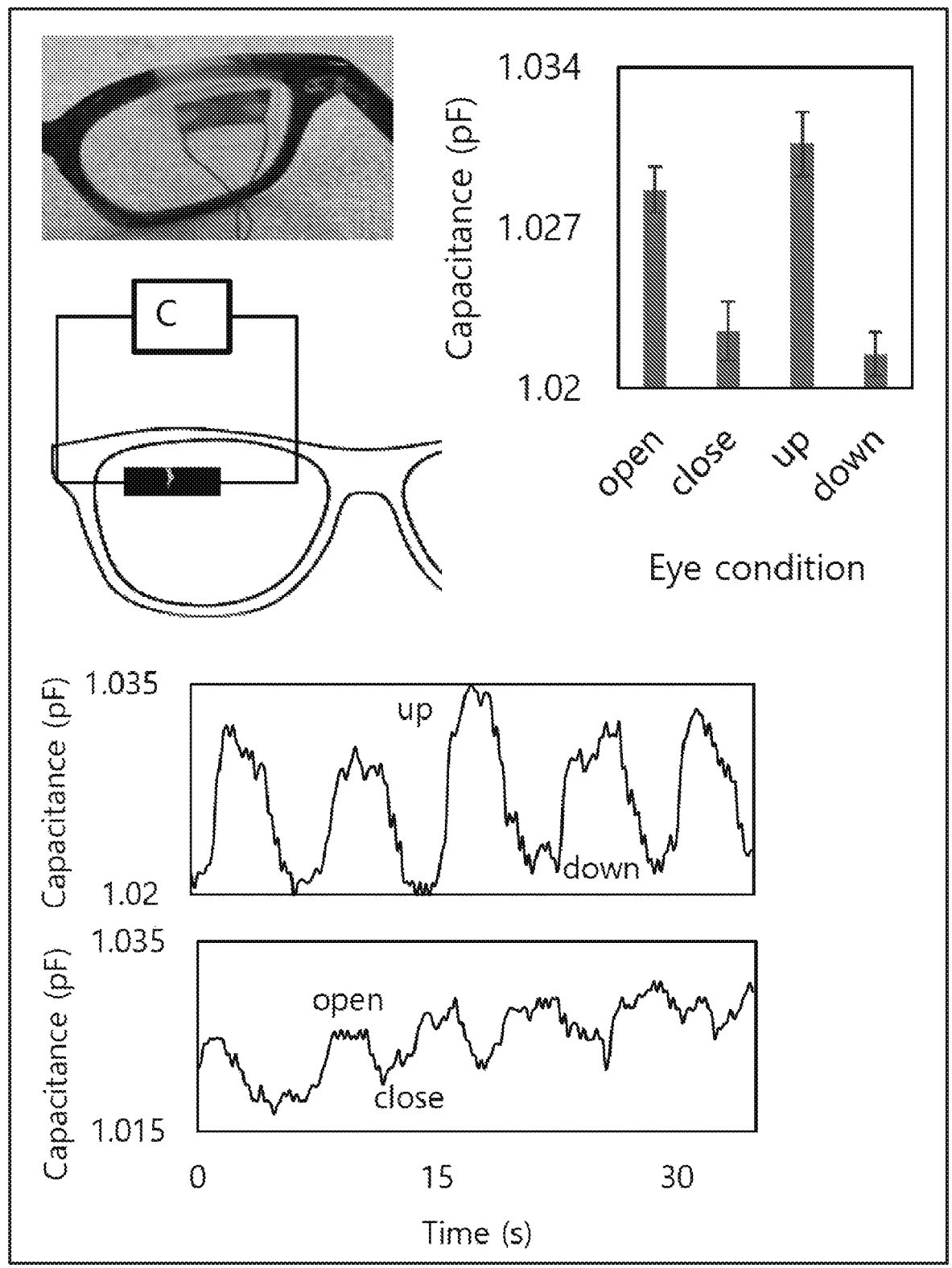

A non-contact capacitive sensor was installed on an eyeglass to detect the eyeball movement (FIG. 5E). The up/down and the open/close movement of an eye can be detected because the distance from the sensor to the eye surface was changed.

Figure 5F:
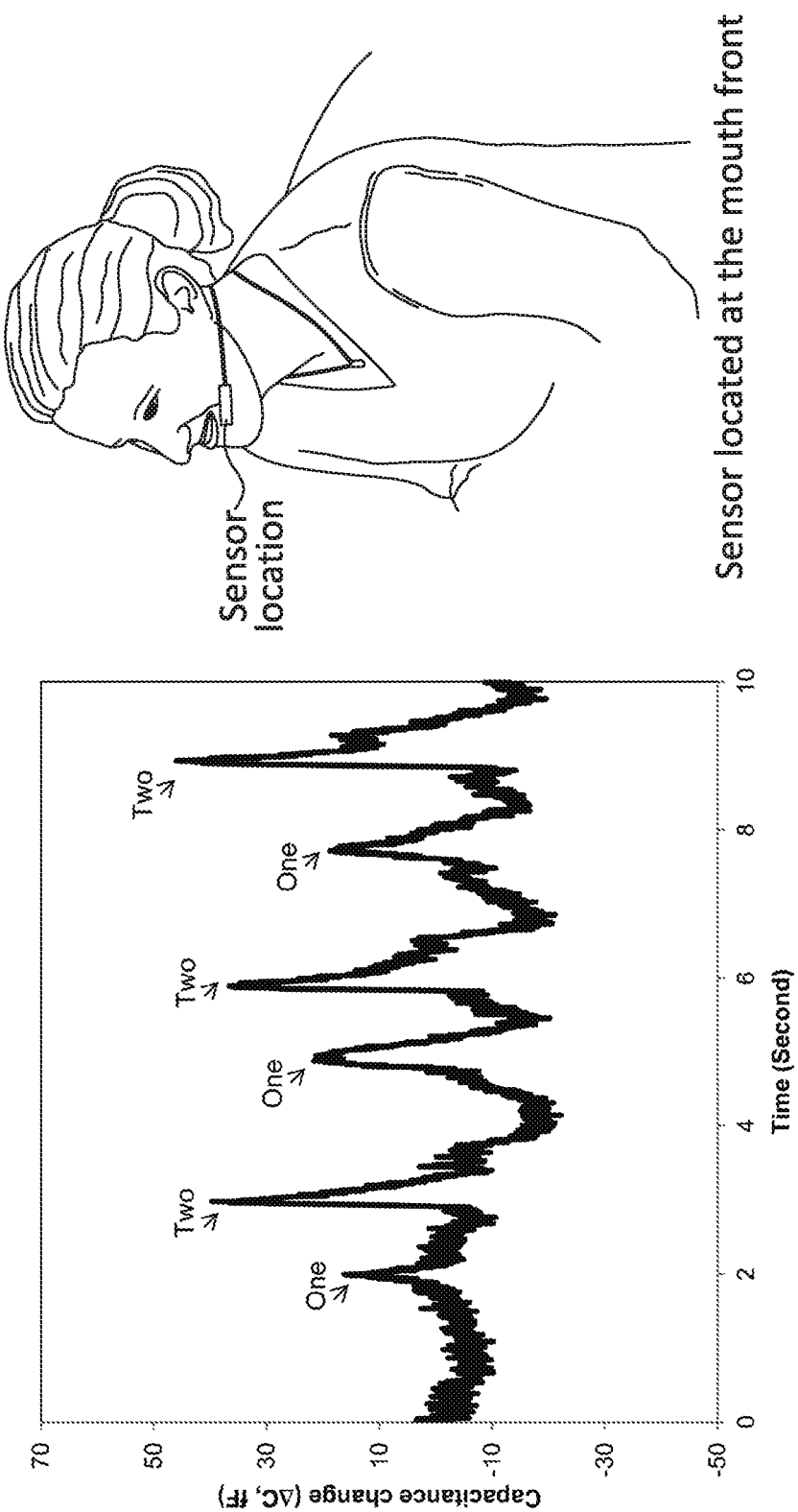

A non-contact capacitive sensor was placed at the front of a subject's mouth to track the lip movement and demonstrated capacitive response to speaking "one" and "two." (FIG. 5F).

To date, various mechanisms and materials have been studied for wearable applications to monitor physical, chemical and biological activities. Among the methods, fracture-induced methods have been developed to fabricate wearable sensors. A composite made of polymer-coated graphene was stretched to induce a crack, which generated a sensitivity. A platinum film was bent to create a crack, which showed a high sensitivity. Compression-induced internal cracks generated piezo-resistive sensitivity. In this study, the composite of MWCNTs and tissue paper was fractured to form crossbar junctions in a crack, which could generate piezo-resistive and piezo-capacitive sensors.

Here, three different types of sensors were demonstrated by controlling the applied pre-strain to CPC. An expected limitation of the sensor fabricated by a pre-strain value is that it could function only in the designed sensing mode, without transforming the sensing mode into another in the sensing process. A fabricated sensor made of a fractured CPC could be fragile. In several embodiments, the sensor was fixed on the paper surface using tape. In several other embodiments, the sensor can be fixed on the paper surface by other means, including infiltrating polymer or other filler materials.

In summary, we present a low cost, flexible, and highly sensitive sensor whose sensitivity is induced by controlled fracture on a MWCNTs-paper composite. By pre-straining, three different sensors are demonstrated as resistive strain sensor, resistive force sensor, and capacitive force and displacement sensors. The piezo-resistive and capacitive sensors can also be fabricated by the reorganized crossing junctions of MWCNT-coated cellulose fibers. The calibration of each sensor showed reliability and repeatability. The sensors attach onto flexible surface such as human skin and are sensitive enough to monitor biological functions including, but not limited to: heart beats, grabbing force, finger motion, and eye movement. These inexpensive and disposable sensors are useful to monitor human behaviors with reliable performance.

While illustrative embodiments have been illustrated and described, it will be appreciated that various changes can be made therein without departing from the spirit and scope of the invention.

The invention claimed is:

1. A sensor, comprising:
a composite substrate comprising a template material comprising a plurality of insulating fibers and a plurality of carbon nanotubes bonded to the insulating fibers forming a nanotube coating on the insulating fibers, the composite substrate having a fracture induced by application of a unidirectional tensile force to the composite substrate, wherein the plurality of insulating fibers form a plurality of crossbar junctions at a site of the fracture; and
a first electrode coupled to the nanotube coating on one side of the fracture and a second electrode coupled to the nanotube coating on an opposite side of the fracture, such that an electrical signal applied between the first electrode and the second electrode passes through the plurality of crossbar junctions at the site of the fracture.

2. The sensor of claim 1, wherein the carbon nanotubes are multi-wall carbon nanotubes.

3. The sensor of claim 1, wherein the insulating fibers are fibers extracted from wood pulp, cotton fibers, synthetic fiber, or a combination thereof.

4. The sensor of claim 1, wherein the composite substrate is formed by applying a composition comprising carbon nanotubes to the template material by capillary action or by chemical binding.

5. The sensor of claim 1, wherein the template material has a thickness in a range of about 0.1 microns to about 10,000 microns.

6. The sensor of claim 1, wherein the template material is a cellulose fiber matrix.

7. The sensor of claim 1, wherein the sensor is an in-plane strain sensor, an out-of-plane piezo-resistive sensor, or a capacitive sensor.

8. The sensor of claim 1, wherein the sensor has a sensor type, determined by the applied strain.

9. The sensor of claim 1, wherein the carbon nanotubes have a diameter in a range of about 0.8 nm to about 200 nm and a length between about 0.1 µm and about 100 µm.

10. The sensor of claim 1, wherein the insulating fibers have a curvature radius larger than 10 µm.

11. The sensor of claim 1, wherein the electrodes are prepared from electrically conductive epoxy.

12. The sensor of claim 1, wherein the electrodes are silver.

13. The sensor of claim 1, wherein the sensor is configured for use to monitor human behavior.

14. The sensor of claim 1, wherein the sensor is a heartbeat sensor, gripping motion sensor, finger movement sensor, eye movement sensor, mouth movement sensor, or abdominal movement sensor.

15. The sensor of claim 1, wherein the sensor is a wearable sensor.

16. The sensor of claim 1, wherein the sensor is a disposable.

17. The sensor of claim 1, wherein the sensor comprises a substrate material attached to the composite substrate.

18. The sensor of claim 17, wherein the substrate material is paper.

19. A method of making a sensor comprising applying a unidirectional tensile force to a precursor composite substrate thereby inducing a fracture to form a fractured composite substrate, wherein the precursor composite substrate comprises:
- a template material comprising a plurality of insulating fibers;
- a plurality of carbon nanotubes bonded to the insulating fibers forming a nanotube coating on the insulating fibers;
- a first electrode coupled to the nanotube coating on one side of the fracture; and
- a second electrode coupled to the nanotube coating on an opposite side of the fracture; and
- wherein the plurality of insulating fibers form a plurality of crossbar junctions at a site of the fracture.

20. A sensor manufactured by the method of claim 19.

* * * * *

UNITED STATES PATENT AND TRADEMARK OFFICE
CERTIFICATE OF CORRECTION

| | |
|---|---|
| PATENT NO. | : 11,719,585 B2 |
| APPLICATION NO. | : 16/768373 |
| DATED | : August 8, 2023 |
| INVENTOR(S) | : J. Chung et al. |

It is certified that error appears in the above-identified patent and that said Letters Patent is hereby corrected as shown below:

In the Claims

| Column | Line | |
|---|---|---|
| 14 | 56 | change "sensor, eye" to -- sensor, an eye -- |

Signed and Sealed this
Ninth Day of April, 2024

Katherine Kelly Vidal
*Director of the United States Patent and Trademark Office*